(12) United States Patent
Chen et al.

(10) Patent No.: US 12,090,250 B2
(45) Date of Patent: *Sep. 17, 2024

(54) DEMINERALIZED BONE FIBERS AND PREPARATION THEREOF

(71) Applicant: LifeNet Health, Virginia Beach, VA (US)

(72) Inventors: Silvia Chen, Kendall Park, VA (US); Grant Cleavenger, Virginia Beach, VA (US); Dennis Phelps, Chesapeake, VA (US); Evans Wralstad, Virginia Beach, VA (US); Breanne Gjurich, Norfolk, VA (US); Austin Johnson, Virginia Beach, VA (US); Alana Sampson, Virginia Beach, VA (US); Adam Entsminger, Virginia Beach, VA (US); Jingsong Chen, Virginia Beach, VA (US)

(73) Assignee: LifeNet Health, Virginia Beach, VA (US)

( * ) Notice: Subject to any disclaimer, the term of this patent is extended or adjusted under 35 U.S.C. 154(b) by 478 days.

This patent is subject to a terminal disclaimer.

(21) Appl. No.: 17/321,904

(22) Filed: May 17, 2021

(65) Prior Publication Data

US 2021/0268147 A1    Sep. 2, 2021

Related U.S. Application Data

(63) Continuation of application No. 16/309,505, filed as application No. PCT/US2017/037265 on Jun. 13, 2017.

(Continued)

(51) Int. Cl.
*A61L 27/36* (2006.01)
*A61K 35/32* (2015.01)

(52) U.S. Cl.
CPC .......... *A61L 27/3608* (2013.01); *A61K 35/32* (2013.01); *A61L 27/365* (2013.01); *A61L 27/3687* (2013.01); *A61L 2430/02* (2013.01)

(58) Field of Classification Search
CPC .. A61F 2/28; A61F 2/4644; A61F 2/42; A61L 27/3608
See application file for complete search history.

(56) References Cited

U.S. PATENT DOCUMENTS

| 5,275,954 A | 1/1994 | Wolfinbarger et al. |
| 5,298,254 A * | 3/1994 | Prewett ................ A61F 2/2846 |
| | | 514/777 |

(Continued)

FOREIGN PATENT DOCUMENTS

| WO | 2014130953 A1 | 8/2014 |
| WO | 2015054547 A1 | 4/2015 |

OTHER PUBLICATIONS

Birkedal-Hansen, H., J. Histochemistry and Cytochemistry, 22(6):434-41 (1974).

(Continued)

*Primary Examiner* — Jason-Dennis N Stewart
(74) *Attorney, Agent, or Firm* — Matney Legal Group PLLC

(57) ABSTRACT

The present invention provides demineralized bone fibers exhibiting optimal handling properties (e.g., high moldability and low elastic modulus) and biological activities (e.g., osteoinductivity) as well as non-demineralized bone fibers useful for preparing the demineralized bone fibers. A well-controlled demineralization process for preparing the demineralized bone of fibers is also provided. Products comprising the demineralized bone fibers and uses thereof are further provided.

35 Claims, 10 Drawing Sheets

Related U.S. Application Data

(60) Provisional application No. 62/349,509, filed on Jun. 13, 2016, provisional application No. 62/351,501, filed on Jun. 17, 2016.

(56) References Cited

U.S. PATENT DOCUMENTS

| | | |
|---|---|---|
| 5,314,476 A | 5/1994 | Prewett et al. |
| 5,507,813 A | 4/1996 | Dowd et al. |
| 5,510,396 A | 4/1996 | Prewett et al. |
| 5,556,379 A | 9/1996 | Wolfinbarger |
| 5,797,871 A | 8/1998 | Wolfinbarger |
| 5,820,581 A | 10/1998 | Wolfinbarger |
| 5,976,104 A | 11/1999 | Wolfinbarger |
| 5,977,034 A | 11/1999 | Wolfinbarger |
| 5,977,432 A | 11/1999 | Wolfinbarger et al. |
| 6,024,735 A | 2/2000 | Wolfinbarger |
| 6,189,537 B1 * | 2/2001 | Wolfinbarger, Jr. ........................ A61F 2/4644 623/901 |
| 6,200,347 B1 | 3/2001 | Anderson et al. |
| 6,305,379 B1 | 10/2001 | Wolfinbarger |
| 6,534,095 B1 | 3/2003 | Moore-Smith et al. |
| 6,830,763 B2 | 12/2004 | O'Leary et al. |
| 7,582,309 B2 | 9/2009 | Rosenberg et al. |
| 7,744,597 B2 | 6/2010 | Gaskins et al. |
| 8,197,474 B2 | 6/2012 | Scarborough et al. |
| 8,337,780 B2 | 12/2012 | Gaskins et al. |
| 9,289,452 B2 | 3/2016 | Shi |
| 9,308,292 B2 | 4/2016 | Winterbottom et al. |
| 10,531,957 B2 | 1/2020 | McAllister et al. |
| 2005/0043814 A1 | 2/2005 | Kusanagi et al. |
| 2005/0283255 A1 | 12/2005 | Geremakis et al. |
| 2010/0196333 A1 | 8/2010 | Gaskins et al. |
| 2012/0143347 A1 * | 6/2012 | Wang .................. A61L 27/3821 623/23.61 |
| 2013/0316012 A1 | 11/2013 | Gaskins et al. |
| 2014/0287006 A1 | 9/2014 | Malessa et al. |
| 2015/0306278 A1 | 10/2015 | McKay |
| 2016/0361171 A1 | 12/2016 | Wang et al. |
| 2018/0311407 A1 * | 11/2018 | Swieszkowski ........ A61L 27/56 |

OTHER PUBLICATIONS

Carpenter et al., Am. J. Orthop., 35(12):562-67 (2006).
Figueiredo et al., Chem. Eng. Research and Design, 89:116-24 (2011).
Horneman et al., AIChE Journal, 50(11):2682-90 (2004).
International Search Report and Written Opinion for International Application No. PCT/US2017/037265, dated Aug. 31, 2017, 10 pages.
Lewandrowski et al., J. Biomedical Materials Research, 31:365-72 (1996).
Makarewicz et al., J. Photographic Science, 28:177-84 (1980).
Meng et al., Scientific Reports, vol. 5, Article No. 17802 (21 pages) (2015).
Optimum DBM Putty, LifeNet Health, www.AccessLifeNetHealth. org, (2 pages) (2013).
Pietrzak et al., Cell Tissue Bank, 12:81-8 (2011).
Pietrzak et al., Cell Tissue Bank, 13:653-61 (2012).
Entire patent prosecution history of U.S. Appl. No. 16/309,505, filed Dec. 13, 2018, entitled, "Demineralized Bone Fibers and Preparation Thereof.".

* cited by examiner

A.

B.

DEMINERALIZED BONE FIBERS AND PREPARATION THEREOF

CROSS-REFERENCE TO RELATED APPLICATIONS

This application is a Continuation of U.S. application Ser. No. 16/309,505, filed Dec. 13, 2018, which is a U.S. National Phase Application of International Application No. PCT/US2017/037265, filed Jun. 13, 2017, claiming the benefit of U.S. Provisional Application No. 62/349,509, filed Jun. 13, 2016, and U.S. Provisional Application No. 62/351,501, filed Jun. 17, 2016, the contents of each of which are incorporated herein by reference in their entireties for all purposes.

FIELD OF THE INVENTION

The invention relates generally to demineralized bone fibers and preparation thereof.

BACKGROUND OF THE INVENTION

While autologous bone grafts are ideal for bone grafting, bone allografts and bone graft substitutes have become widely used due to the limited availability and potential complications of autologous bone grafts. Demineralized bone matrix is an autograft, allograft or xenograft bone product prepared by removing inorganic minerals from bone and leaving a matrix containing mainly collagen, by a process called demineralization. The demineralized bone matrix has superior biological properties (e.g., osteoinductivity) to non-demineralized bone because growth factors such as bone morphogenetic proteins (BMPs) in the bone become exposed and accessible to cells in vivo or in vitro and retain biological activities upon demineralization.

The demineralized bone matrix is generally prepared by, for example, acidification of allograft bone to remove minerals and expose growth factors. Among the demineralized bone matrix products commercially available, many of them fail to provide desirable handling properties (e.g., moldability and cohesiveness) and biological activities (e.g., optimal osteoinductivity and growth factor presence/activation), due to lack of good control on the balance of sufficient demineralization and optimal bio-active growth factor retention. There remains a need for bone fibers with an optimal size range in combination with a well-controlled demineralization process to prepare demineralized bone matrix products having optimal handling properties and biological activities.

SUMMARY OF THE INVENTION

The present invention relates to demineralized bone fibers, which are also referred to herein as demineralized bone matrix (DBM) or DBM fibers, as well as methods for preparing the demineralized bone fibers from a non-demineralized bone graft, for example, non-demineralized bone fibers (also known as mineralized bone fibers), and uses of the demineralized bone fibers.

A method for preparing a demineralized bone graft is provided. The demineralized bone graft has a residual calcium content of less than 6 wt % based on the dry weight of the demineralized bone graft. The preparation method comprises subjecting a non-demineralized bone graft to a single incubation in an acid solution for no more than 300 seconds. The acid solution has a pH of 0-4.

The non-demineralized bone graft may comprise bone fibers, bone particles, bone sheets, bone cubes, bone shafts, or a combination thereof. For example, the non-demineralized bone graft may comprise non-demineralized bone fibers that form demineralized bone fibers. The non-demineralized bone fibers may have an average shortest dimension of less than 200 μm. The non-demineralized bone fibers may be generated by a Computer Numerical Control (CNC) machine using a chip load of 0.004"-0.011".

The demineralized bone fibers may be osteoinductive.

The demineralized bone fibers may have an elastic modulus of less than 100.00 kPa.

The preparation method may further comprise adding an effective amount of a buffer to the acid solution after the single incubation. The pH of the resulting solution may be adjusted to 2.5-7 within 90 seconds after the buffer addition.

The preparation method may further comprise storing the demineralized bone fibers in a storage solution, and the storage solution may be glycerol, a buffer, or a cryopreservation solution.

The preparation method may further comprise drying the demineralized bone fibers.

The preparation method may further comprise releasing at least 75 wt % of calcium in the non-demineralized bone fibers.

The preparation method may further comprise retaining at least 1 ng of a bone morphogenetic protein (BMP) per gram of the non-demineralized bone fibers, based on the dry weight of the non-demineralized bone fibers, and the BMP may be selected from the group consisting of BMP-2, BMP-3, BMP-4, BMP-5, BMP-6, BMP-7, BMP-8, BMP-9, BMP-10, BMP-11, BMP-12, BMP-13, BMP-14, BMP-15 and a mixture thereof.

A composition comprising demineralized bone fibers is also provided.

The composition may comprise the demineralized bone fibers produced by the preparation method of the invention.

The composition may comprise demineralized bone fibers having a residual calcium content of less than 6 wt % based on the dry weight of the demineralized bone fibers, and the demineralized bone fibers may be osteoinductive and may have an elastic modulus of less than 100.00 kPa.

The composition may further comprise viable cells. The viable cells may be selected from the group consisting of bone cells, bone forming cells, osteoprogenitor cells, stem cells and a combination thereof.

The composition may further comprise a non-demineralized bone particulate, and the non-demineralized bone particulate may comprise viable bone cells. The non-demineralized bone particulate may be selected from the group consisting of a cancellous particulate, a cortical bone particulate, a cortical-cancellous particulate and a combination thereof.

The demineralized bone fibers in the composition may be cryopreserved, frozen, or sterilized.

An implant is further provided. The implant comprises the composition according to the invention. The implant may further comprise a synthetic material. The implant may further comprise a bone particle or particulate.

A package is further provided. The package comprises the composition according to the invention. The package may be a jar, a pouch, tray or syringe.

A method for promoting osteoinductivity, osteoconductivity, chondroinductivity, chondroconductivity, or fibrochondral differentiation in entheses is provided. The method comprises incubating cells with an effective amount of the composition according to the invention. The method may further comprise forming a bone tissue. The cells may be located at a defective site in a subject before the incubation. Where the cells are at a defective site in a subject, for example, before implantation of the composition, the method may further comprise forming a bone tissue at the defective site. The cells may be in a tissue culture before the incubation.

A method for promoting cell attachment, proliferation, maintaining a differentiation state or preventing de-differentiation of cells is provided. The method comprises incubating cells with an effective amount of the composition according to the invention.

A method for promoting osteogenesis, chondrogenesis, or fibrocartilage tissue genesis in cells is provided. The method comprises incubating the cells with an effective amount of the composition according to the invention.

A method for treating a tissue or organ defect in a subject is provided. The method comprises applying to the site of the defect an effective amount of the composition according to the invention.

The invention provides a composition comprising demineralized bone fibers having a residual calcium content of between 0.5-6 wt % based on the dry weight of the demineralized bone fibers, in which the demineralized bone fibers are osteoinductive. The demineralized bone fibers may have an average shortest dimension of less than 200 µm. The demineralized bone fibers may have a specific surface area of at least 100 $cm^2/g$. The demineralized bone fibers may have an elastic modulus of less than 100 kPa.

DETAILED DESCRIPTION OF THE INVENTION

The present invention relates to demineralized bone fibers, which are also referred to herein as demineralized bone matrix (DBM) or DBM fibers. The demineralized bone fibers of the present invention exhibit optimal handling properties (e.g., high moldability and low elastic modulus) and biological activities (e.g., osteoinductivity). The demineralized bone fibers may be in an optimal size range and exhibit desirable handling property with or without bone particles or synthetic material based particles. The non-demineralized bone fibers may be used in a well-controlled demineralization process for preparing desirable demineralized bone fibers with an optimal balance between retention and exposure of growth factors and differentiating factors. The demineralized bone fibers are suitable for various uses. Unless stated otherwise, all wt % figures herein are relative to the total composition.

According to one aspect of the present invention, demineralized bone fibers and non-demineralized bone fibers are provided.

Figure 1:
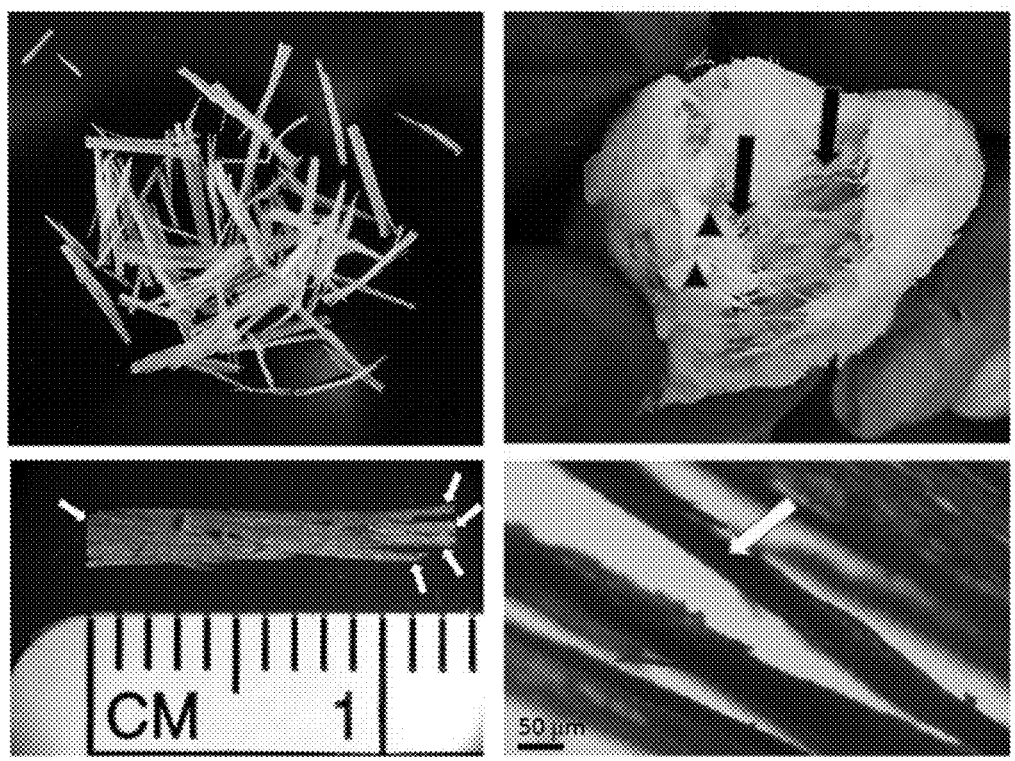
FIG. 1 shows images of non-demineralized bone fibers (top left panel), one individual non-demineralized bone fiber (bottom left) having bone filaments (white arrows in bottom left panel and in bottom right panel, magnified view under microscope, scale bar=50 µm), and demineralized bone fibers having filaments (top right panel, black arrows) mixed with bone particles (top right panel, black triangles). The ruler shown in the bottom left panel is in centimeters.

The term "bone fiber" as used herein refers to a fiber made from a bone tissue by, for example, cutting or milling the bone tissue using a computer numerical control (CNC) machine, or shaving or cutting, as described in U.S. Pat. No. 7,744,597. A bone fiber has an elongated main body whose longest dimension (i.e., length) is substantially greater than the other dimensions by, for example, about at least 5, 10, 50, 100, 500 or 1000 times or in a range of about 5-1,000, 10-500 or 50-200 times. The bone fiber may have one or more bone microfibers. The bone fiber may have or split into at least about 1, 5, 10, 20, 50, 100, 200, 500 or 1,000 bone filaments (FIG. 1).

The term "microfiber" as used herein refers to a projection or spike extending from the main body of a bone fiber. The longest dimension (i.e., length) of a microfiber is the length of the microfiber, i.e., from the tip of the projection or spike to where the projection or spike connects to the main body of the bone fiber. The length of the microfiber is greater than the other dimensions by, for example, about at least 5, 10, 50 or 100 times. The length of the microfiber is less than about 10%, 9%, 8%, 7%, 6%, 5%, 4%, 3%, 2%, 1%, 0.5%, 0.25% or 0.1% of the length of the bone fiber.

The term "bone filament" as used herein refers to a slender threadlike element in a bone fiber. A bone fiber may be split into multiple bone filaments along its length. The length of a bone filament in a bone fiber is the same or shorter than the length of the bone fiber, for example, at least about 10%, 20%, 30%, 40%, 50%, 60%, 70%, 80%, 90%, 95% or 99% of the length of the bone fiber. The width of the bone filament is shorter than the width of the bone fiber, for example, less than about 50%, 40%, 30%, 20%, 10%, 9%, 8%, 7%, 6%, 5%, 4%, 3%, 2%, 1%, 0.5%, 0.25%, 0.1%, 0.001% or 0.0001% of the width of the bone fiber. The cross section area of a bone filament in a bone fiber may be less than about 50%, 40%, 30%, 20%, 10%, 9%, 8%, 7%, 6%, 5%, 4%, 3%, 2%, 1%, 0.5%, 0.25%, 0.1%, 0.001%, 0.0001% or 0.00001% of cross section area of the bone fiber. The bone filament may or may not be at the edge of the bone fiber. In some embodiments, the bone fiber may be shattered into bone filaments along the length of the bone fiber by, for example, absorbing a mechanical impact during the cutting or milling process. In other embodiments, the direction of the cutting or milling may be in parallel with the bone Haversian canals of a long bone. In yet other embodiments, the direction of the cutting or milling may be vertical to the bone Haversian canals of a long bone.

The bone tissue may be of any source. For example, the bone tissue may be a cortical bone, a cancellous bone or a cortico-cancellous bone. The bone tissue may be obtained from an animal, for example, a mammal. The mammal may be a human, a cow, a pig, a dog, a cat, a non-human primate, a rodent such as a rat or mouse, a horse, a goat, a sheep or a deer. The animal may be alive or non-living. For example, the bone tissue may be obtained from a living human donor, a human cadaveric donor, or a living or non-living animal.

The term "demineralization" as used herein refers to a process during which inorganic minerals (e.g., hydroxyapatite) are removed from a non-demineralized bone graft leaving a matrix consisting mainly of collagen, also known as demineralized bone matrix (DBM). The term "non-demineralized bone graft" used herein refers to a material comprising a piece of natural bone. The non-demineralized bone graft may comprise bone fibers, bone particles, bone sheets, bone cubes, bone shafts, or a combination thereof. The non-demineralized bone graft may comprise viable cells, which may be selected from the group consisting of bone cells, bone forming cells, osteoprogenitor cells, stem cells or a combination thereof. In one embodiment, the non-demineralized bone graft comprises non-demineralized bone fibers and viable cells. Where the non-demineralized bone graft comprises bone fibers, demineralized bone fibers may be obtained after demineralization of the non-demineralized bone graft.

Demineralization may be achieved by exposing bone fibers to an acid solution. Demineralized bone fibers are bone fibers that have been subject to demineralization. Non-demineralized (or mineralized) bone fibers are bone fibers that have not been subject to demineralization. Upon demineralization, calcium is released from the non-demineralized bone fibers. The extent of demineralization may be characterized based on the content (wt %) of the residual calcium in the demineralized bone fibers, for example, based on the dry weight of the demineralized bone fibers.

The demineralized bone fibers of the present invention may have a residual calcium content of less than about 8 wt % (e.g., about 8 wt %, 7 wt %, 6 wt %, 5 wt %, 4 wt %, 3 wt %, 2 wt %, 1 wt %, 0.5 wt %, 0.1 wt % or 0.01 wt %), less than about 6 wt % (e.g., in the range of about 0.001-6 wt %, 0.1-6 wt %, 0.5-1 wt %, 0.5-2 wt %, 0.5-3 wt %, 0.5-4 wt %, 0.5-5 wt %, 0.5-6 wt %, 0.5-7 wt %, 0.5-8 wt %, 1-6 wt %, 2-6 wt %, 2-5 wt %, 0.01-0.5 wt %, 0.5%-1 wt %, 1-2 wt %, 2-3 wt %, 3-4 wt %, 4-5 wt % or 5-6 wt %), less than about 4 wt % (e.g., about 0.5-3 wt %), based on the dry weight of the demineralized bone fibers. For example, the demineralized bone fibers may have a residual calcium content of less than about 6 wt % (e.g., about 0.3-3.5 wt %), based on the dry weight of the demineralized bone fibers.

The demineralized bone fiber may have or split into at least about 1, 5, 10, 20, 50, 100, 200, 500 or 1,000 demineralized bone filaments. The non-demineralized bone fiber may have or split into at least about 1, 5, 10, 20, 50, 100, 200, 500 or 1,000 bone filaments. Upon demineralization of bone fiber, the number of filaments in the bone fiber or split from the bone fiber may be increased by at least about 10%, 20%, 30%, 40%, 50%, 60%, 70%, 80%, 90%, 95%, 100%, 150%, 200% or 500%.

The demineralized bone fibers may be highly moldable with a low elasticity. The terms "moldable" or "moldability" used herein refer to the capability of the demineralized bone fibers to be deformed, i.e., to change their size and/or shape. The terms "elasticity" and "elastic" used herein refer to the capability of the demineralized bone fibers to recover their size and/or shape after being molded or deformed (e.g., being stretched or compressed). The demineralized bone fibers may have an elastic modulus (also known as modulus of elasticity, tensile modulus or Young's modulus) of less than about 500, 400, 300, 200, 150, 100, 50 or 10 kPa, or in a range of about 10-500, 10-200 or 50-100 kPa.

The demineralized bone fibers and derivative products thereof may be cohesive after being wetted with a liquid and molded, by hand or otherwise, into a desirable mass or shape. The term "cohesive" or "cohesiveness" as used herein refers to the capability of demineralized bone fibers or derivative products thereof to retain at least a predetermined portion of an initial mass (e.g., at least about 10, 20, 30, 40, 50, 60, 70, 80, 90 or 95% by weight) or shape (e.g., volume) (e.g., at least about 10, 20, 30, 40, 50, 60, 70, 80, 90 or 95% by volume) for a predetermined period of time in a predetermined environment. The molded mass may be picked up and handled without losing a substantial portion (e.g., losing at least about 10, 20, 30, 40, 50, 60, 70, 80, 90 or 95 wt %) of its mass. The predetermined period of time may be about 1, 5, 10, 30, 45 seconds, 1, 5, 10, 30, 60, 120, 180, 240 or 480 minutes, for example, about 10, 60 or 180 minutes. The predetermined environment may be a liquid environment. For example, the demineralized bone fibers may be in contact with or submerged by a liquid. The weight ratio between the demineralized bone fibers and the liquid may be in the range between about 1:0.5 and 1:1,000, for example, between about 1:1 to 1:100. The volume ratio between the demineralized bone fibers and the liquid may be in the range between about 1:0.5 and 1:1,000, for example, between about 1:1 and 1:100. The liquid may be a buffer (e.g., saline), blood, or a combination thereof. The aqueous solution may be still or flowing at a speed of, for example, about 5-500 rpm or 1-60,000 mm per minute.

Alternatively, the cohesiveness of the demineralized bone fibers may be determined by measuring biomechanical properties such as elasticity, plasticity via strain/deformation, and/or compression, tensile, shear stress testing, or volume expansion after hydration.

The demineralized bone fibers may be cohesive in the absence of a binder or a cross-linking agent. Examples of binders include glycerol (e.g., Preservon®), acidic solutions (e.g., lactic and trifluoroacetic acid), buffering solutions (e.g., phosphate), and adhesive binders (e.g., fibrin glues, bone cements or liquefied bone). The cross-linking agent may be selected from the group consisting of 1-Ethyl-3-(3-dimethylaminopropyl)carbodiimide (EDC), EDC/hyaluronic acid, genipin, hyaluronic acid and glutaraldehyde. The demineralized bone fibers may be cohesive with a binder as above. In one embodiment, the demineralized bone fibers may be combined and stored with glycerol. In another embodiment, the demineralized bone fibers may be combined and stored with hyaluronic acid.

The demineralized bone fibers may be cohesive when a small amount of pressure is applied to the demineralized bone fibers. The small amount of pressure may range from about 1 Pa to about 100 Pa, from about 100 Pa to about 1,000 Pa, from about 1 kPa to about 10 kPa, form about 10 KPa to about 50 kPa, from about 50 kPa to about 100 kPa or from about 100 kPa to 1 MPa. The pressure may be applied to the demineralized bone fibers by mechanical force, with or without a device.

The demineralized bone fibers may have a longest dimension (i.e., length), a shortest dimension (i.e., thickness) and a remaining dimension (i.e., width). The demineralized bone fibers may have an average length in the range between about 100 microns and about 100 mm, between about 100 μm and about 50 mm, about 5-30 mm, about 15-25 mm or about 15-20 mm, for example, about 20 mm; an average width may be in the range between about 5 microns and about 5 mm; and an average thickness (i.e., an average shortest dimension) may be less than about 250 μm, 200 μm, 150 μm, 100 μm, or 50 μm, or may be in the range of about 5-5,000 μm, 5-10 μm, 5-25 μm, 5-50 μm, 5-75 μm, 5-100 μm, 5-200 μm, 10-25 μm, 10-50 μm, 10-75 μm, 10-100 μm, 10-200 μm, 10-300 μm, 10-450 μm, 25-50 μm, 25-75 μm, 25-100 μm, 25-150 μm, 25-200 μm, 25-300 μm, 25-450 μm, 50-75 μm, 50-100 μm, 50-250 μm, 50-300 μm, 50-450 μm, 50-1,000 μm, 100-500 μm or 150-250 μm, for example, about 75 μm.

The demineralized bone fibers may be osteoinductive. The demineralized bone fibers may contain no viable cells. The demineralized bone fibers may be mixed with viable cells or a non-demineralized bone particulate comprising viable cells to prepare a composition such as a derivative product. The viable bone cells may be selected from the group consisting of bone forming cells, bone cells, osteoprogenitor cells, stem cells or a combination thereof. In some embodiments, the volume ratio between the non-demineralized bone particulate containing viable bone cells and the demineralized bone fibers in a derivative product is in the weight range from about 1:1 to about 4:1, from about 1.5:1 to about 3:1, from about 1:1 to about 3:1, or from about 1.5:1 to about 2.5:1, for example, about 2:1. The non-demineralized bone particulate containing viable cells may be a cancellous particulate, a cortical bone particulate, a cortical-cancellous particulate, or a combination thereof. The derivative product may be cohesive.

The volume of demineralized bone fibers may be measured by using a measuring tool by manually placing into a space of a predefined volume, optionally with pressure. The measured demineralized bone fibers may be compacted to the extent such that there are no visible void spaces present. The measured demineralized bone fibers and a non-demineralized bone particulate (e.g., a cancellous particulate, a cortical bone particulate, a cortico-cancellous particulate) may be placed into a pouch simultaneously or sequentially to make a composition such as a derivative product.

The demineralized bone fibers may contain collagen, osteocalcin, osteonectin, bone sialo protein, osteopontin, BMPs such as BMP-2, 4, and 7, IGF-1, and TGF-b, and mixtures thereof.

In one embodiment, the compact demineralized bone fibers outlined previously may be packaged with or without a liquid, with or without freeze-drying, and/or stored at an ambient temperature (e.g., about 20-25° C.).

The demineralized bone fibers of the present invention may be in an implant or a package. The demineralized bone fibers may be stored in a storage solution. The storage solution may be glycerol, a buffer or a cryopreservation solution. The package may be a jar, a pouch with or without a port, tray or syringe. The demineralized bone fibers may be optionally sterilized. The demineralized bone fibers may be cryopreserved or frozen or stored at an ambient room temperature (e.g., about 20-25° C.).

The demineralized bone fibers may be mixed with another tissue such as cortico-cancellous particulates. In some cases, these two components may be frozen in one package with a clear separation between the two processed tissue types. Where the components are frozen, the package is preferably thawed quickly. The solution used for packaging the tissue may be removed, and replaced with a fresh rinsate solution for removing any residual components from the tissue. After the rinsate is removed, the two tissue components may then be removed simultaneously from the package. At this point, the two components may be mixed manually to create a homogenous mixture in a desirable mass or shape. Oftentimes, this mixing may be done in a basin, and may require supplementing the tissue with an additional solution to increase the ease of mixing and handling of the two components as a single product.

The demineralized or non-demineralized bone fibers of the present invention may have a predetermined specific surface area. The term "specific surface area" used herein refers to the total surface area of the demineralized or non-demineralized bone fibers per unit of mass or volume of the demineralized or non-demineralized bone fibers. The specific surface area of the demineralized or non-demineralized bone fibers may be measured by conventional techniques known in the art. The specific surface area may be measured in an adsorption based method, in which the demineralized or non-demineralized bone fibers may be exposed to an absorbate molecule (i.e., a probe molecule) under a predetermined condition for a predetermined period of time before quantifying the amount of the probe molecule absorbed to the demineralized or non-demineralized bone fibers.

For example, the specific surface area of the demineralized or non-demineralized bone fibers may be determined by protein adsorption or gas sorption method. The specific surface area of the demineralized or non-demineralized bone fibers may be at least about 20, 50, 100, 150, 200, 250, 500, 750 or 1,000 $cm^2/g$ or at least about 10, 37, 50, 100, 150, 200, 250, 500, 750 or 1,000 $cm^2/cm^3$. The specific surface area of the demineralized or non-demineralized bone fibers may be in the range of about 20-20,000 $cm^2/g$, 20-100 $cm^2/g$, 20-200 $cm^2/g$, 100-200 $cm^2/g$, 100-300 $cm^2/g$, 100-400 $cm^2/g$, 100-500 $cm^2/g$, 100-600 $cm^2/g$, 200-500 $cm^2/g$, 300-500 $cm^2/g$, 300-1000 $cm^2/g$, 500-1,000 $cm^2/g$, 1,000-3,000 $cm^2/g$, 3,000-10,000 $cm^2/g$, 10,000-20,000 $cm^2/g$, 50-100 $cm^2/g$, 50-200 $cm^2/g$, 50-300 $cm^2/g$, 75-300 $cm^2/g$, 200-400 $cm^2/g$ or 300-1,000 $cm^2/g$. The specific surface area of the demineralized or non-demineralized bone fibers may be in the range of about 1-5 $cm^2/cm^3$, 1-10 $cm^2/cm^3$, 5-10 $cm^2/cm^3$, 10-20 $cm^2/cm^3$, 10-30 $cm^2/cm^3$, 10-40 $cm^2/cm^3$, 10-50 $cm^2/cm^3$, 10-60 $cm^2/cm^3$, 10-100 $cm^2/cm^3$, 50-150 $cm^2/cm^3$, 75-125 $cm^2/cm^3$, 37-37,000 $cm^2/cm^3$, 37-185 $cm^2/cm^3$, 37-370 $cm^2/cm^3$, 185-925 $cm^2/cm^3$, 370-925 $cm^2/cm^3$, 555-925 $cm^2/cm^3$, 925-1,850 $cm^2/cm^3$, 1,850-5,550 $cm^2/cm^3$, 5,550-18,500 $cm^2/cm^3$, 18,500-37,000 $cm^2/cm^3$, 92.5-185 $cm^2/cm^3$, 139-555 $cm^2/cm^3$, 370-740 $cm^2/cm^3$ or 555-1,850 $cm^2/cm^3$.

The non-demineralized bone fibers may have a longest dimension (i.e., length), a shortest dimension (i.e., thickness) and a remaining dimension (i.e., width). The non-demineralized bone fibers may have an average length in the range of about 0.1-100 mm, about 0.1-50 mm, about 5-30 mm, about 15-25 mm or about 15-20 mm, for example, about 20 mm; an average width in the range between about 5-5,000 μm; and an average thickness (i.e., the shortest dimension) may be less than about 250 μm, 200 μm, 150 μm, 100 μm, or 50 μm, or in the range of about 5-5,000 μm, 5-10 μm, 5-25 μm, 5-50 μm, 5-75 μm, 5-100 μm, 5-200 μm, 10-25 μm, 10-50 μm, 10-75 μm, 10-100 μm, 10-200 μm, 10-300 μm, 10-450 μm, 25-50 μm, 25-75 μm, 25-100 μm, 25-150 μm, 25-200 μm, 25-300 μm, 25-450 μm, 50-75 μm, 50-100 μm, 50-250 μm, 50-300 μm, 50-450 μm, 50-1,000 μm, 100-500 μm or 150-250 μm, for example, about 75 μm.

The non-demineralized bone fibers are capable of releasing calcium upon a single incubation in an acid solution for a predetermined short period of time. The acid solution may have a pH of about 0-4, 0-3, 0-2 or 0-1. The acid solution may be any strong acid solution, for example, 0.5 M or 1.0 M hydrochloric acid. Examples of the acids may include hydrochloric acid, nitric acid, sulfuric acid. At least about 10%, 20%, 30%, 40%, 50%, 60%, 70%, 75%, 80%, 90%, 91%, 92%, 93%, 94%, 95%, 96%, 97%, 98%, 99% or 99.9% by weight of calcium may be released from the non-demineralized bone fibers upon the incubation. The predetermined short period of time may be no more than about 900, 750, 600, 450, 300, 250, 200, 180, 150, 120, 90, 60, 40 30, 20, 10 or 5 seconds. In one embodiment, the non-demineralized bone fibers are capable of releasing at least about 75 wt % calcium in 1 M hydrochloric acid in no more than about 300 seconds.

The non-demineralized bone fibers are capable of becoming demineralized bone fibers having a predetermined residual calcium content upon a single incubation in an acid solution for a predetermined short period of time. The acid solution may have a pH of about 0-4, 0-3, 0-2 or 0-1. The acid solution may be any strong acid solution, for example, 0.5 M or 1.0 M (or 1.0 N) hydrochloric acid. Examples of the acids may include hydrochloric acid, nitric acid, sulfuric acid. The predetermined residual calcium content may be less than about 8 wt % (e.g., about 8 wt %, 7 wt %, 6 wt %, 5 wt %, 4 wt %, 3 wt %, 2 wt %, 1 wt %, 0.75 wt %, 0.5 wt %, 0.25 wt %, 0.1 wt % or 0.01 wt %), less than about 6 wt %, less than about 4 wt % (e.g., about 0.5-3 wt %), based on the dry weight of the demineralized bone fibers. For example, the demineralized bone fibers may have a residual calcium content of less than about 6 wt % (e.g., about 0.3-3.5 wt %), based on the dry weight of the demineralized bone fibers. The predetermined short period of time may be no more than about 900, 750, 600, 450, 300, 250, 200, 180, 150, 120, 90, 60, 40 30, 20, 10 or 5 seconds. In one embodiment, the non-demineralized bone fibers are capable of becoming demineralized bone fibers having a residual calcium content of less than 6 wt % upon a single incubation in 1 M hydrochloric acid for no more than about 300 seconds.

The non-demineralized bone fibers are capable of retaining a growth factor or a differentiation factor such as an osteogenic growth factor that is entrapped with bone mineral, upon incubation in an acid solution for a predetermined short period of time. Examples of growth factors are bone morphogenetic proteins (BMPs) and insulin-like growth factor (IGF). Examples of BMPs include BMP-2, BMP-3, BMP-4, BMP-5, BMP-6, BMP-7, BMP-8, BMP-9, BMP-10, BMP-11, BMP-12, BMP-13, BMP-14, BMP-15, any truncated or modified forms of BMP-2, BMP-3, BMP-4, BMP-5, BMP-6, BMP-7, BMP-8, BMP-9, BMP-10, BMP-11, BMP-12, BMP-13, BMP-14, or BMP-15, and a mixture thereof. At least about 10%, 20%, 30%, 40%, 50%, 60%, 70%, 80%, 90%, 95%, 99% or 99.9% by weight or at least about 0.001, 0.01, 0.5, 1, 5, 10, 50, 100, 500 or 1,000 ng of a growth factor or differentiation factor may be retained per gram of the non-demineralized bone fibers, based on the dry weight of the non-demineralized bone fibers, upon incubation in an acid solution for no more than about 900, 750, 600, 450, 300, 250, 200, 180, 150, 120, 90, 60, 40, 30, 20, 10 or 5 seconds. The acid solution may have a pH of about 0-4, 0-3, 0-2 or 0-1. The acid solution may be any strong acid solution, for example, 0.5 M or 1.0 M hydrochloric acid. Examples of the acids may include hydrochloric acid, nitric acid, sulfuric acid. For example, the non-demineralized bone fibers may be capable of retaining at least about 1 ng of a bone morphogenetic protein (BMP) per gram of the dry non-demineralized bone fibers upon a single incubation in an acid solution for no more than about 300 seconds, wherein the BMP is selected from the group consisting of BMP-2, BMP-3, BMP-4, BMP-5, BMP-6, BMP-7, BMP-8, BMP-9, BMP-10, BMP-11, BMP-12, BMP-13, BMP-14, BMP-15 and a mixture thereof.

The non-demineralized bone fibers may be generated by various methods. For example, the non-demineralized bone fibers are generated from a bone tissue by a Computer Numerical Control (CNC) machine using a predetermined cutting or milling program. The cutting program may include a chip load of about 0.002"-0.012" or 0.003"-0.012"

(e.g., about 0.002-0.003", 0.004-0.012", 0.003", 0.006", 0.009" or 0.012"). In one embodiment, the chip load is 0.009". Cutters of different length (e.g., about 0.5 cm to 30 cm, 0.5 cm, 1 cm, 1.5 cm, 2 cm, 3 cm, 4 cm, 5 cm, 6 cm, 7 cm, 8 cm, 9 cm, 10 cm, 15 cm, 20 cm, 25 cm or 30 cm), number of flutes or torque may be used to cut or mill the bone tissue. Before cutting or milling, the moisture of the bone tissue may be modified by, for example, drying or freeze-drying to decrease the moisture level or incubation with a liquid to increase the moisture level. The non-demineralized bone fibers may be generated by other methods such as shaving, slicing, or cutting as described in U.S. Pat. Nos. 7,744,597 and 5,314,476, and PCT International Application Publication No. WO/2015/054547.

According to another aspect of the present invention, a method for preparing a demineralized bone graft is provided. The preparation method comprises subjecting a non-demineralized bone graft to a single incubation in an acid solution for a predetermined short period of time. This preparation method is called single pulse acid demineralization (SPAD). The resulting demineralized bone graft has a calcium content of less than about 8 wt % (e.g., about 8 wt %, 7 wt %, 6 wt %, 5 wt %, 4 wt %, 3 wt %, 2 wt %, 1 wt %, 0.75 wt %, 0.5 wt %, 0.25 wt %, 0.1 wt % or 0.01 wt %), less than about 6 wt %, less than about 4 wt % (e.g., about 0.5-3 wt %), based on the dry weight of the demineralized bone graft. For example, the demineralized bone graft may have a residual calcium content of less than about 6 wt % (e.g., about 0.3-3.5 wt %), based on the dry weight of the demineralized bone graft. The non-demineralized bone graft may comprise bone fibers, bone particles, bone sheets, bone cubes, bone shafts, or a combination thereof. In one embodiment, the non-demineralized bone graft comprises non-demineralized bone fibers and the demineralized bone graft comprises demineralized bone fibers.

The acid solution may have a pH of about −0.3-0, 0-4, 0-3, 0-2 or 0-1. The acid solution may be any strong acid solution, for example, 0.5 M or 1.0 M, 1.2 M, 1.5M, 2.0 M hydrochloric acid. Examples of the acids may include hydrochloric acid, nitric acid, sulfuric acid. The predetermined short period of time may be no more than about 2700, 1800, 1500, 1200, 900, 750, 600, 450, 300, 250, 200, 180, 150, 120, 90, 60, 40, 30, 20, 10 or 5 seconds, for example, about 30-150, 120-140 or 120-150 seconds.

To make demineralized bone fibers, a non-demineralized bone graft may be processed by pulsatile acid demineralization (PAD), as disclosed in U.S. Pat. Nos. 6,534,095 and 8,337,780, or by continued acid demineralization (CAD), as disclosed in U.S. Pat. Nos. 6,189,537, 5,275,954, and 6,830, 763. The PAD and CAD differ from the SPAD. The SPAD of the present invention subjects a non-demineralized bone graft to a single incubation with an acid solution for a very short period of time, for example, no more than 300 seconds, for the total acid exposure time of SPAD process. The PAD subjects a non-demineralized bone graft to multiple incubations with an acid solution, each incubation lasting for at least approximately 5 minutes, and it takes a long period of time to complete the entire PAD process. The CAD subjects a non-demineralized bone graft to a single incubation with an acid solution for a long period of time, for example, roughly 300 minutes or more, for the entire CAD process.

The SPAD preparation method may further comprise a quick stop of the acid incubation by raising the pH of the acid solution. For example, an effective amount of a buffer may be added to raise the pH of the acid solution within a short period of time, for example, within about 300, 250, 200, 180, 150, 120, 90, 80, 60, 40, 30, 20, 10 or 5 seconds, or within about 5-300, 10-200 or 50-100 seconds. The resulting solution may have a pH of about 2.5-7, 3-7, 4-7, 4.5-7, 2.5-6.5, 3-6.5, 4-6.5, 5-6.5, 2.5-5, 3-5, 4-5, 2.5-4 or 3-4. The buffer may be a sodium glycinate buffer, a citrate buffer, a phosphate buffer, a carbonate buffer, a TRIS buffer or an acetate buffer having a concentration at, for example, about 10 M, 9 M, 8 M, 7 M, 6 M, 5 M, 4 M, 3 M, 2 M, 1 M or 0.5 M. A tissue culture medium, for example, Dulbecco's Modified Eagle Medium (DMEM), RPMI, or (Minimum Essential Media) MEM, may be added after the acid/buffer solution is removed and the tissue is rinsed with saline, or used as the buffer solution to stop the acid incubation.

In one embodiment, the SPAD preparation method comprises subjecting non-demineralized bone fibers to a single incubation in an acid solution having a pH of 0-4, and then adding an effective amount of a buffer to the acid solution at the end of the incubation. In another embodiment, the pH of the resulting solution may be adjusted to 2.5-7 within 90 seconds of buffer addition to the solution.

The preparation method may further comprise storing the resulting demineralized bone fibers in a storage solution. The storage solution may be glycerol, a buffer or a cryopreservation solution. The demineralized bone fibers may be stored at room temperature. During storage, the demineralized bone fibers may retain a significant level of, for example, at least about 50%, 60%, 70%, 80%, 90%, 95%, 99% or 99.9% of their characteristics or properties. For example, a substantial level of elastic modulus, cohesiveness or a biological activity (e.g., BMP activity) of the demineralized bone fiber may be maintained during storage. The demineralized bone fibers may be optionally sterilized before storage. The demineralized bone fibers may be stored at an ambient room temperature (e.g., about 20-25° C.), cryopreserved or frozen.

The preparation method may further comprise drying the demineralized bone fibers. For example, the demineralized bone fibers may be freeze dried. The demineralized bone fiber may have a water activity (Aw) of less than about 0.5, 0.3 or 0.1.

The preparation method may further comprise releasing at least about 70%, 75%, 80%, 85%, 90%, 93%, 94%, 95%, 96%, 97%, 98%, 99% or 99.9% by weight, for example, at least about 75 wt % of calcium from the non-demineralized bone fibers.

The preparation method may further comprise retaining at least a growth factor or differentiation factor from the non-demineralized bone fibers. At least about 10%, 20%, 30%, 40%, 50%, 60%, 70%, 80%, 90%, 95%, 99% or 99.9% by weight of the non-demineralized bone fibers, based on the dry weight of the non-demineralized bone fibers, may be exposed. Alternatively, at least about 0.001, 0.01, 0.5, 1, 5, 10, 50, 100, 500 or 1,000 ng of the growth factor or differentiation factor may be retained per gram of the non-demineralized bone fibers, based on the dry weight of the non-demineralized bone fibers. The growth factor or differentiation factor may be retained upon a single incubation of the non-demineralized bone fibers in an acid solution for a predetermined time period, for example, no more than about 900, 750, 600, 450, 300, 250, 200, 180, 150, 120, 90, 60, 40, 30, 20, 10 or 5 seconds. The acid solution may have a pH of about 0-4, 0-3, 0-2 or 0-1. The acid solution may be any strong acid solution, for example, 0.5 M or 1.0 M hydrochloric acid. Examples of the acids may include hydrochloric acid, nitric acid, sulfuric acid. In one embodiment, the preparation method further comprises retaining at least about 1 ng of a bone morphogenetic protein (BMP)

from gram of the non-demineralized bone fibers, based on the dry weight of the non-demineralized bone fibers, upon a single incubation in an acid solution for no more than about 300 seconds, wherein the BMP is selected from the group consisting of BMP-2, BMP-3, BMP-4, BMP-5, BMP-6, BMP-7, BMP-8, BMP-9, BMP-10, BMP-11, BMP-12, BMP-13, BMP-14, BMP-15 and a mixture thereof.

The preparation method of the present invention may be used to produce the demineralized bone fibers of the present invention from the non-demineralized bone fibers of the present invention.

According to the preparation method of the present invention, the demineralized bone fibers as produced may have a residual calcium content of less than about 8 wt % (e.g., about 8 wt %, 7 wt %, 6 wt %, 5 wt %, 4 wt %, 3 wt %, 2 wt %, 1 wt %, 0.5 wt %, 0.1 wt % or 0.01 wt %), less than about 6 wt % (e.g., in the range of about 0.001-6 wt %, 0.1-6 wt %, 0.5-6 wt %, 1-6 wt %, 2-6 wt %, 2-5 wt %, 0.01-0.5 wt %, 0.5%-1 wt %, 1-2 wt %, 2-3 wt %, 3-4 wt %, 4-5 wt % or 5-6 wt %) or less than about 4 wt % (e.g., about 0.5-3 wt %), based on the dry weight of the demineralized bone fibers. For example, the demineralized bone fibers may have a residual calcium content of less than about 6 wt % (e.g., about 0.3-3.5 wt %), based on the dry weight of the demineralized bone fibers.

The demineralized bone fibers as produced may be cohesive, for example, in the absence of a binder or a cross-linking agent, and without applying a pressure to the demineralized bone fibers. The demineralized bone fibers as produced may have a longest dimension (i.e., length), a shortest dimension (i.e., thickness) and a remaining dimension (i.e., width). The demineralized bone fibers may have an average length in the range of about 0.1-100 mm, 0.1-50 mm, 5-30 mm, 15-25 mm or 15-20 mm, for example, about 20 mm; an average width in the range between about 5-5,000 Nm; and an average thickness (or an average shortest dimension) may be less than about 250 μm, 200 μm, 150 μm, 100 μm, or 50 μm, or in the range of about 5-5,000 μm, 5-10 μm, 5-25 μm, 5-50 μm, 5-75 μm, 5-100 μm, 5-200 μm, 10-25 μm, 10-50 μm, 10-75 μm, 10-100 μm, 10-200 μm, 10-300 μm, 10-450 μm, 25-50 μm, 25-75 μm, 25-100 μm, 25-150 μm, 25-200 μm, 25-300 μm, 25-450 μm, 50-75 μm, 50-100 μm, 50-250 μm, 50-300 μm, 50-450 μm, 50-1,000 μm, 100-500 μm or 150-250 μm, for example, about 75 μm.

The demineralized bone fibers as produced may be osteoinductive. The demineralized bone fibers may contain no viable cells, for example, viable bone cells. The demineralized bone fibers may be mixed with viable cells or a non-demineralized bone particulate containing viable cells, for example, viable bone cells or bone forming cells. In some embodiments, the volume ratio between the non-demineralized bone particulate containing viable bone cells and the demineralized bone fibers is in the range from about 1:1 to about 4:1, from about 1.5:1 to about 3:1, from about 1:1 to about 3:1, or from about 1.5:1 to about 2.5:1, for example, about 2:1. The non-demineralized bone particulate containing viable cells may be a cancellous particulate, a cortical bone particulate, a cortical-cancellous particulate, or a combination thereof.

The demineralized bone fibers as produced may be easily molded and have a low elastic modulus. The demineralized bone fibers may have an elasticity modulus of less than about 500, 400, 300, 200, 150, 100, 50 or 10 kPa, or in a range of about 10-500, 10-200 or 50-100 kPa.

The non-demineralized bone fibers suitable for use in the preparation method of the present invention may have specific surface area of at least about 20 or 200 cm$^2$/g or at least about 37 cm$^2$/cm$^3$. The specific surface area of the non-demineralized bone fibers may be in the range of about 20-20,000 cm$^2$/g, 20-100 cm$^2$/g, 20-200 cm$^2$/g, 100-200 cm$^2$/g, 100-300 cm$^2$/g, 100-400 cm$^2$/g, 100-500 cm$^2$/g, 100-600 cm$^2$/g, 200-500 cm2/g, 300-500 cm$^2$/g, 300-1000 cm$^2$/g, 500-1,000 cm$^2$/g, 1,000-3,000 cm$^2$/g, 3,000-10,000 cm$^2$/g, 10,000-20,000 cm$^2$/g, 50-100 cm$^2$/g, 50-200 cm$^2$/g, 50-300 cm$^2$/g, 75-300 cm$^2$/g, 200-400 cm$^2$/g or 300-1,000 cm$^2$/g. The specific surface area of the non-demineralized bone fibers may be in the range of about 1-5 cm$^2$/cm$^3$, 1-10 cm$^2$/cm$^3$, 5-10 cm$^2$/cm$^3$, 10-20 cm$^2$/cm$^3$, 10-30 cm$^2$/cm$^3$, 10-40 cm$^2$/cm$^3$, 10-50 cm$^2$/cm$^3$, 10-60 cm$^2$/cm$^3$, 10-100 cm$^2$/cm$^3$, 50-150 cm$^2$/cm$^3$, 75-125 cm$^2$/cm$^3$, 37-37,000 cm$^2$/cm$^3$, 37-185 cm$^2$/cm$^3$, 37-370 cm$^2$/cm$^3$, 185-925 cm$^2$/cm$^3$, 370-925 cm$^2$/cm$^3$, 555-925 cm$^2$/cm$^3$, 925-1,850 cm$^2$/cm$^3$, 1,850-5,550 cm$^2$/cm$^3$, 5,550-18,500 cm$^2$/cm$^3$, 18,500-37,000 cm$^2$/cm$^3$, 92.5-185 cm$^2$/cm$^3$, 139-555 cm$^2$/cm$^3$, 370-740 cm$^2$/cm$^3$ or 555-1,850 cm$^2$/cm$^3$.

The non-demineralized bone fibers may have a longest dimension (i.e., length), a shortest dimension (i.e., thickness) and a remaining dimension (i.e., width). The non-demineralized bone fibers may have an average length in the range of about 0.1-100 mm, about 0.1-50 mm, about 5-30 mm, about 15-25 mm or about 15-20 mm, for example, about 20 mm; an average width in the range of about 5-5,000 μm; and an average thickness (i.e., the shortest dimension) may be less than about 250 μm, 200 μm, 150 μm, 100 μm, or 50 μm, or in the range of about 5-5,000 μm, 5-10 μm, 5-25 μm, 5-50 μm, 5-75 μm, 5-100 μm, 5-200 μm, 10-25 μm, 10-50 μm, 10-75 μm, 10-100 μm, 10-200 μm, 10-300 μm, 10-450 μm, 25-50 μm, 25-75 μm, 25-100 μm, 25-150 μm, 25-200 μm, 25-300 μm, 25-450 μm, 50-75 μm, 50-100 μm, 50-250 μm, 50-300 μm, 50-450 μm, 50-1,000 μm, 100-500 μm or 150-250 μm, for example, about 75 μm.

The non-demineralized bone fibers suitable for use in the preparation method of the present invention may be capable of releasing calcium upon a single incubation in an acid solution for a predetermined short period of time. The acid solution may have a pH of about 0-4, 0-3, 0-2 or 0-1. The acid solution may be any strong acid solution, for example, 0.5 M or 1.0 M hydrochloric acid. Examples of the acids may include hydrochloric acid, nitric acid, sulfuric acid. At least about 10%, 20%, 30%, 40%, 50%, 60%, 70%, 75%, 80%, 85%, 90%, 91%, 92%, 93%, 94%, 95%, 96%, 97%, 98%, 99% or 99.9% by weight of calcium may be released from the non-demineralized bone fibers upon the incubation. The predetermined short period of time may be no more than about 900, 750, 600, 450 300, 250, 200, 180, 150, 120, 90, 60, 40, 30, 20, 10 or 5 seconds.

The non-demineralized bone fibers suitable for use in the preparation method of the present invention may be capable of retaining a growth factor or a differentiation factor such as an osteogenic growth factor that is entrapped with bone mineral, upon incubation in an acid solution for a predetermined short period of time. The acid solution may have a pH of about 0-4, 0-3, 0-2 or 0-1. The acid solution may be any strong acid solution, for example, 0.5 M or 1.0 M hydrochloric acid. Examples of the acids may include hydrochloric acid, nitric acid, sulfuric acid. Examples of growth factors are bone morphogenetic proteins (BMPs) and insulin like growth factor (IGF). Examples of BMPs include BMP-2, BMP-3, BMP-4, BMP-5, BMP-6, BMP-7, BMP-8, BMP-9, BMP-10, BMP-11, BMP-12, BMP-13, BMP-14, BMP-15, any truncated or modified forms of BMP-2, BMP-3, BMP-4, BMP-5, BMP-6, BMP-7, BMP-8, BMP-9, BMP-10, BMP-11, BMP-12, BMP-13, BMP-14, or BMP-15, and a mixture thereof. At least about 10%, 20%, 30%, 40%, 50%, 60%, 70%, 80%, 90%, 95%, 99% or 99.9% by weight, or at least about 0.001, 0.01, 0.5, 1, 5, 10, 50 or 100 ng of a growth factor or differentiation factor may be retained per gram of the non-demineralized bone fibers, based on the dry weight of the non-demineralized bone fibers, upon incubation in an acid solution for no more than about 900, 750, 600, 450, 300, 250, 200, 180, 150, 120, 90, 60, 40, 30, 20, 10 or 5 seconds. For example, the non-demineralized bone fibers may be capable of retaining at least about 1 ng of a bone morphogenetic protein (BMP) per gram of the dry non-demineralized bone fibers upon a single incubation in an acid solution for no more than about 300 seconds, wherein the BMP is selected from the group consisting of BMP-2, BMP-3, BMP-4, BMP-5, BMP-6, BMP-7, BMP-8, BMP-9, BMP-10, BMP-11, BMP-12, BMP-13, BMP-14, BMP-15 and a mixture thereof.

The non-demineralized bone fibers suitable for use in the preparation method of the present invention may be generated by, for example, a Computer Numerical Control (CNC) machine using a predetermined cutting program. The cutting program may include a chip load of about 0.002"-0.012" (e.g., about 0.002-0.003", 0.004-0.012", 0.003", 0.006", 0.009" or 0.012"). In one embodiment, the chip load is 0.009". The non-demineralized bone fibers may be generated by other methods such as shaving, slicing, or cutting as described in U.S. Pat. Nos. 7,744,597 and 5,314,476, and PCT International Application Publication No. WO/2015/054547.

For each preparation method, the demineralized bone fibers as produced are provided. Suitable non-demineralized bone fibers are also provided.

According to yet another aspect of the present invention, a composition, implant or package comprising demineralized bone fibers is provided.

A composition comprising the demineralized bone fibers of the present invention is provided. The demineralized bone fibers may be prepared by the SPAD method of the present invention.

The composition may comprise osteoinductive demineralized bone fibers, which have a residual calcium content of less than about 8 wt % (e.g., about 8 wt %, 7 wt %, 6 wt %, 5 wt %, 4 wt %, 3 wt %, 2 wt %, 1 wt %, 0.5 wt %, 0.1 wt % or 0.01 wt %), less than about 6 wt % (e.g., in the range of about 0.001-6 wt %, 0.1-6 wt %, 0.5-6 wt %, 1-6 wt %, 2-6 wt %, 2-5 wt %, 0.01-0.5 wt %, 0.5%-1 wt %, 1-2 wt %, 2-3 wt %, 3-4 wt %, 4-5 wt % or 5-6 wt %), less than about 4 wt % (e.g., about 0.5-3 wt %), based on the dry weight of the demineralized bone fibers, and an elastic modulus of less than about 500, 400, 300, 200, 150, 100, 50 or 10 kPa, or in a range of about 10-500, 10-200 or 50-100 kPa. In one embodiment, the composition comprises osteoinductive demineralized bone fibers, which have a residual calcium content of less than about 4 wt %, based on the dry weight of the demineralized bone fibers, and an elastic modulus of less than about 100 kPa.

The composition may further comprise a pharmaceutically acceptable carrier or diluent. Carriers, diluents and excipients suitable in the pharmaceutical composition are well known in the art.

The composition may further comprise viable cells and/or a non-demineralized bone particulate containing viable cells. The non-demineralized bone particulate may comprise viable cells. The viable cells may be selected from the group consisting of bone cells, bone forming cells, osteoprogenitor cells, stem cells or a combination thereof. The volume ratio between the non-demineralized bone particulate and the demineralized bone fibers may be in the range from about 1:1 to about 4:1, from about 1.5:1 to about 3:1, from about 1:1 to about 3:1, or from about 1.5:1 to about 2.5:1, for example, about 2:1. The non-demineralized bone particulate may be a cancellous particulate, a cortical bone particulate, a cortico-cancellous particulate, or a combination thereof.

The composition may further comprise a bioactive agent. The bioactive agent has a biological activity and may be a chemical compound, a biological molecule or a combination thereof. Examples of the bioactive agent include an osteogenic growth factor, collagen, glycosaminoglycans, osteonectin, bone sialo protein, an osteoinductive factor, a chondrogenic factor, a cytokine, a mitogenic factor, a chemotactic factor, a transforming growth factor (TGF), a fibroblast growth factor (FGF), an angiogenic factor, an insulin-like growth factor (IGF), a platelet-derived growth factor (PDGF), an epidermal growth factor (EGF), a vascular endothelial growth factor (VEGF), a nerve growth factor (NGF), a neurotrophin, a bone morphogenetic protein (BMP), osteogenin, osteopontin, osteocalcin, cementum attachment protein, erythropoietin, thrombopoietin, tumor necrosis factor (TNF), an interferon, a colony stimulating factor (CSF), or an interleukin, among others. The bioactive factor may be a BMP, PDGF, FGF, VEGF, TGF, insulin, among others. Examples of BMPs include BMP-2, BMP-3, BMP-4, BMP-5, BMP-6, BMP-7, BMP-8, BMP-9, BMP-10, BMP-11, BMP-12, BMP-13, BMP-14, BMP-15, any truncated or modified forms of BMP-2, BMP-3, BMP-4, BMP-5, BMP-6, BMP-7, BMP-8, BMP-9, BMP-10, BMP-11, BMP-12, BMP-13, BMP-14, or BMP-15, and a mixture thereof.

The invention provides a composition comprising demineralized bone fibers having a residual calcium content of between 0.5-6 wt % based on the dry weight of the demineralized bone fibers, in which the demineralized bone fibers are osteoinductive. The demineralized bone fibers may have an average shortest dimension of less than about 250 µm, 200 µm, 150 µm, 100 µm, or 50 µm. The demineralized bone fibers may have a specific surface area of at least about 20, 50, 100, 150, 200, 250, 500, 750 or 1,000 $cm^2/g$ or at least about 10, 37, 50, 100, 150, 200, 250, 500, 750 or 1,000 $cm^2/cm^3$. The demineralized bone fibers may have an elastic modulus of less than about 500, 400, 300, 200, 150, 100, 50 or 10 kPa.

An implant comprising the composition of the present invention is provided. The term "implant" as used herein refers to an object designed to be placed partially or wholly within the body of a subject for one or more therapeutic or prophylactic purposes such as for tissue augmentation, contouring, restoring physiological function, repairing or restoring tissues damaged by disease or trauma, and/or delivering therapeutic agents to normal, damaged or diseased organs and tissues. The subject may be a living animal in need of a bone implant, preferably a mammal. The mammal may be a human, a cow, a pig, a dog, a cat, a non-human primate, a rodent such as a rat or mouse, a horse, a goat, a sheep, or a deer. The implant may further comprise synthetic materials or bone particles or particulates.

A package comprising the composition of the present invention is provided. The package may be a jar, pouch with or without a port, tray or syringe. The package may further comprise viable cells and/or a non-demineralized bone particulate. The non-demineralized bone particulate may comprise viable cells. The viable cells may be selected from the group consisting of bone cells, bone forming cells, osteoprogenitor cells, stem cells or a combination thereof. The volume ratio between the non-demineralized bone particulate and the demineralized bone fibers may be in the range from about 1:1 to about 4:1, from about 1.5:1 to about 3:1, from about 1:1 to about 3:1, or from about 1.5:1 to about 2.5:1, for example, about 2:1. The non-demineralized bone particulate may comprise may be selected from the group consisting of a cancellous particulate, a cortical bone particulate, a cortico-cancellous particulate, and a combination thereof. The composition comprising the demineralized bone fibers and the viable bone cells may be placed in two separate compartments in the pouch.

According to a further aspect of the present invention, various uses of the demineralized bone fibers are provided.

The term "an effective amount" refers to an amount of a composition comprising the demineralized bone fibers required to achieve a stated goal (e.g., promoting osteoinductivity, osteoconductivity, chondroinductivity, chondroconductivity, or fibrochondral differentiation in entheses; promoting cell attachment, proliferation, maintaining a differentiation state or preventing de-differentiation of cells; promoting osteogenesis, chondrogenesis, or fibrocartilage tissue genesis in cells; and treating a tissue or organ defect in a subject). The effective amount of the composition comprising the demineralized bone fibers may vary depending upon the stated goals, the physical characteristics of the subject, the nature and severity of the defect, the existence of related or unrelated medical conditions, the nature of the demineralized bone fibers, the composition comprising the demineralized bone fibers, the means of administering the composition to the subject, and the administration route. A specific dose for a given subject may generally be set by the judgment of a physician. The composition may be administered to the subject in one or multiple doses. Each dose may be 0.1 cc, 0.2 cc, 0.5 cc, 1 cc, 2 cc, 5 cc, 10 cc, 20 cc, 30 cc, 50 cc, 100 cc, 200 cc, depends on the implantation site and surgery needs.

A method for promoting osteoinductivity is provided. The method comprises incubating cells with an effective amount of a composition comprising the demineralized bone fibers. The term "osteoinductivity" as used herein refers to the ability of the composition comprising the demineralized bone fibers to cause cells to differentiate into cells that are more osteoblast-like (e.g., in phenotype or in gene and protein expressions), to increase the proliferation of osteoblasts, or both.

A method for promoting osteoconductivity is provided. The method comprises incubating cells with an effective amount of a composition comprising the demineralized bone fibers. The term "osteoconductivity" as used herein refers to the ability of the composition comprising the demineralized bone fibers to accelerate the deposition of new bone or the rate of bone growth.

A method for promoting chondroconductivity is provided. The method comprises incubating cells with an effective amount of a composition comprising the demineralized bone fibers of the present invention. The term "chondroconductivity" as used herein refers to the ability of the composition comprising the demineralized bone fibers to cause cells to differentiate into cells that are more chondrocyte-like (e.g., in phenotype or in gene and protein expressions), or the term may refer to increasing the proliferation of chondrocytes, or both.

A method for promoting chondroconductivity is provided. The method comprises incubating cells with an effective amount of a composition comprising the demineralized bone fibers of the present invention. The term "chondroconductivity" as used herein refers to the ability of the composition comprising the demineralized bone fibers to accelerate the deposition of new cartilage or the rate of cartilage growth.

A method for promoting osteoinductivity, osteoconductivity, chondroinductivity, chondroconductivity or fibrochondral differentiation in entheses is provided. The method comprises incubating cells with an effective amount of a composition comprising the demineralized bone fibers of the present invention. The term "fibrochondral differentiation in entheses" as used herein refers to the ability of the composition comprising the demineralized bone fibers to cause cells to differentiate into cells that are more similar to insertion sites, osteotendinous junctions, osteoligamentous junctions (e.g., in phenotype or in gene and protein expressions.

In the method for promoting osteoinductivity, osteoconductivity, chondroinductivity, chondroconductivity or fibrochondral differentiation in entheses, the cells may be undifferentiated or partially differentiated cells before the contact with the demineralized bone fibers. The cells may be incubated in culture or in a tissue, organ or portion thereof or in an organism before being in contact with the demineralized bone fibers.

The method for promoting osteoinductivity, osteoconductivity, chondroinductivity, chondroconductivity or fibrochondral differentiation in entheses may further comprise forming a bone tissue. Where the cells are at a defective site in a subject, the method may further comprise forming a bone tissue at the defective site.

To assess osteoinductivity, chondroinductivity, or fibrochondral differentiation in entheses, the presence a relevant marker in cells, either in vitro (e.g., cell or tissue culture) or in vivo (i.e., tissue samples from a subject) may be used. For example, cells express alkaline phosphatases during the early stages of differentiation toward osteoblast lineages. Therefore, in vitro alkaline phosphatase (AP) assays may be used to evaluate osteoinductivity in cells cultured on the composition described herein. The ability of the composition of the present invention to stimulate or induce the alkaline phosphatase expression in an otherwise non-bone forming cells, such as myoblast (C2C12 cells), would indicate that the composition of the present invention has osteoinductive activity. In these assays, cells cultured on other composition without the properties described herein are used as negative controls to show that the baseline alkaline phosphatase expression on non-bone forming cells. The baseline of the osteoblastic markers in the negative control need not be zero, meaning that the cells in the negative control group may have at least some level of phenotypic marker(s). The BMP activity (e.g., BMP-2, BMP-3, BMP-4, BMP-5, BMP-6, BMP-7, BMP-8, BMP-9, BMP-10, BMP-11, BMP-12, BMP-13, BMP-14, BMP-15, any truncated or modified forms of BMP-2, BMP-3, BMP-4, BMP-5, BMP-6, BMP-7, BMP-8, BMP-9, BMP-10, BMP-11, BMP-12, BMP-13, BMP-14, or BMP-15) may also be used as a biomarker for osteoinductivity. Accordingly, an "osteoinductive" composition of the present invention would simply cause an increase in the osteoblastic markers in experimental cells over control grown on the other compositions. Similarly, chondrocyte markers, including but not limited to type X collagen, type II collagen, Sox 9, Aggrecan. Matrilin-1 and CEP-68, to name a few, may be used to assess chondroinductive potential. Moreover, markers for fibrochondral differentiation in entheses may include collagen type I, collagen type II and aggrecan.

Osteoinductivity, chondroinductivity, and fibrochondral differentiation in entheses may be determined in tissue culture by investigating the ability of the composition of the present invention to differentiate or induce osteoblast phenotype, chondrocyte phenotype, entheses cell phenotype in cultured cells, such as primary cells, cell lines, or explants. For example, the cells may display increased production of a marker characteristic of osteoblasts and/or chondrocytes, such as alkaline phosphatase (AP) or phosphorylated SMAD, etc. For example, the osteoinductive, chondroinductive, or fibrochondral differentiation potentials of the composition described herein may be more than 0.2, 0.4, 0.6, 0.8, 1, 2, 3, 4, 5, 6, 7, 8, 9 or 10 times greater than the control compositions and/or implants. In another example, the osteoinductive, chondroinductive, entheses potentials of the culture on the composition and/or implant described herein may be more than 10, 20, 30, 40, 50, 60, 70, 80, 90, 100, 500 or even 1000 times greater than those of the control composition and/or implant.

Osteoinductivity, chondroinductivity and fibrochondral differentiation in entheses may be used for assessing bone, cartilage, or fibrocartilage tissue forming potential induced by the composition and/or implant of the present invention in a location such as muscle, may also be evaluated using a suitable animal model. For example, intermuscular implantation between a rodent biceps femoris and gluteus superficialis muscles has been used as a model to assess osteoinductive activity of bioactive factors.

A method for promoting cell attachment, proliferation, maintaining a differentiation state or preventing de-differentiation of cells is provided. The method comprises incubating cells with an effective amount of the composition of the present invention. The cells may be selected from the group consisting of osteoblasts, chondrocytes, and fibrocartilage tissue cells.

A method for promoting osteogenesis, chondrogenesis, or fibrocartilage tissue genesis in entheses in cells is provided. The method comprises incubating cells with an effective amount of the composition of the present invention. The term "osteogenesis" as used herein refers to the deposition new bone material or formation of new bone, including, but not limited to, intramembranous osteogenesis and endochondral osteogenesis. The term "chondrogenesis" as used herein refers to the deposition of new cartilage material or formation of new cartilage. The term "fibrocartilage tissue genesis" as used herein refers to the deposition new fibrocartilage material or formation of a new fibrocartilage tissue. Examples of the cells may include cells in any tissue in which bone, cartilage, or fibrocartilage tissue formation is desired.

A method for treating a tissue or organ defect or injury in subject is provided. The method comprises incubating cells with an effective amount of the composition of the present invention. The tissue or organ defect may be a musculoskeletal, dental or soft-tissue defect or injury. Examples of the defect include osseous defects and defects in cartilage, entheses, spinal disk, and tendon insertion site to bone. The subject may be a living animal in need of a bone implant, preferably a mammal. The mammal may be a human, a cow, a pig, a dog, a cat, a non-human primate, a rodent such as a rat or mouse, a horse, a goat, a sheep, or a deer.

In some embodiments, the cells are progenitor cells or adult (or somatic) stem cells. In additional embodiments, the progenitor cells or the adult stem cells are derived from placenta, bone marrow, adipose tissue, blood vessel, amniotic fluid, synovial fluid, synovial membrane, pericardium, periosteum, dura, peripheral blood, umbilical blood, menstrual blood, baby teeth, nucleus pulposus, brain, skin, hair follicle, intestinal crypt, neural tissue, or muscle, or differentiated from a pluripotent cell type (embryonic stem cell, induced pluripotent stem cell) into a somatic stem cell type such as those from the aforementioned sources, or with cells coursed from transdifferentiated or directly differentiated cells, such as by way of converting a fibroblast directly to a mesenchymal stem cell or to a somatic cell such as an osteoblast.

The term "about" as used herein when referring to a measurable value such as an amount, a percentage, and the like, is meant to encompass variations of ±20% or ±10%, ±5%, ±1%, or ±0.1% from the specified value, as such variations are appropriate.

Example 1. Generation of Non-Demineralized Bone Fibers

Debrided cortical bone was cut into desired dimensions using Computer Numerical Control (CNC) machining. The fibers were treated or in some cases not treated with Allowash® processing technologies as described previously in, for example, U.S. Pat. Nos. 5,556,379, 5,976,104, 6,024,735, 5,797,871, 5,820,581, 5,977,034, and 5,977,432 for cleaning and disinfection. Samples were made from different milling programs having a chip load of 0.003", 0.006", 0.009", or 0.012", and cutters with straight or helix flutes and different cutter lengths (0.5", 0.75" or other lengths). The number of flutes were 2, 4 or 6. The milling was done at room temperature with or without cooling the cutter. FIG. 1 shows images of the non-demineralized bone fibers having bone filaments (top left, bottom left and bottom left panels).

Example 2. Production of Demineralized Bone Fibers

Figure 2:
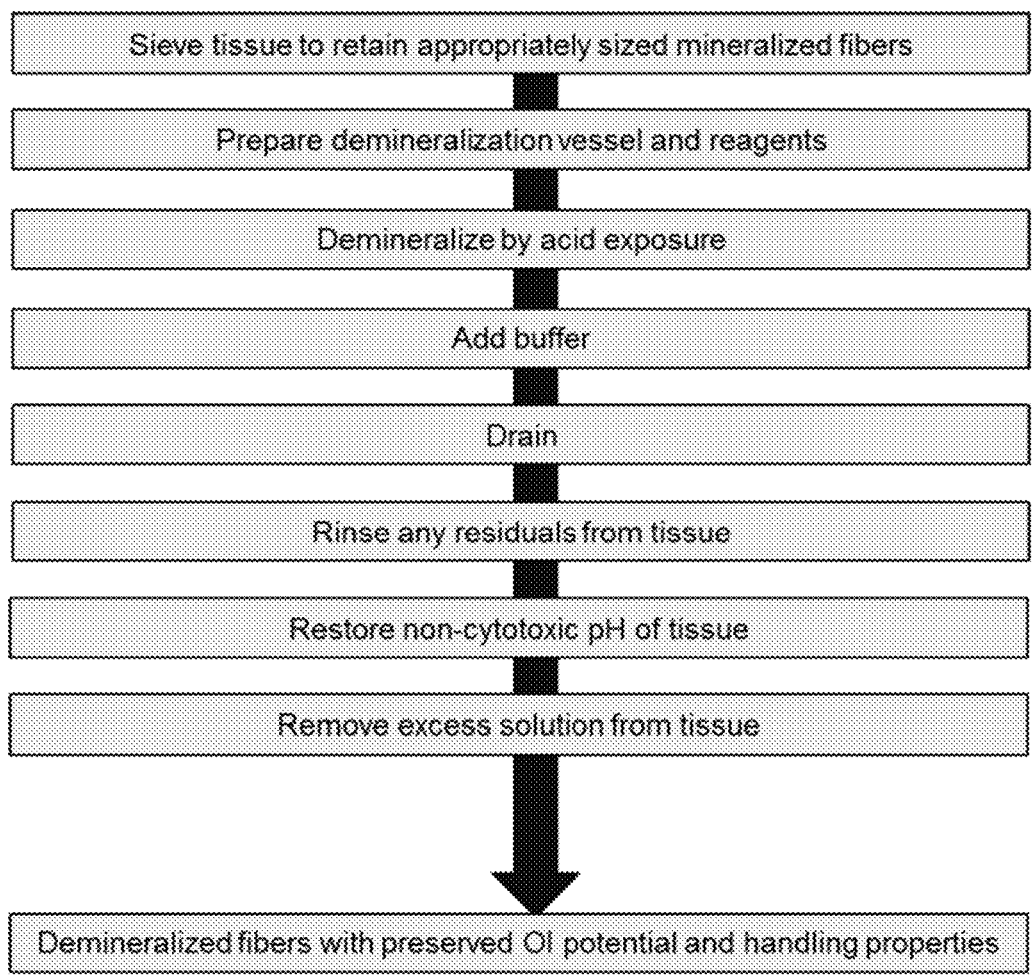
FIG. 2 shows an example of a single pulse acid demineralization process (SPAD).

Demineralized bone fibers were produced from mineralized (or non-demineralized) cortical bone fibers by single pulse acid demineralization (SPAD) as described in FIG. 2. Mineralized bone fibers were generated from a bone tissue of a donor as described in Example 1, and then loaded into a demineralization vessel. 1 M HCl was added into the vessel and demineralization started with vigorous shaking. A buffer was then added to the vessel followed by shaking. The vessel was quickly drained to remove the solution in the vessel. The demineralized bone fibers were then subjected to several saline rinses with vigorous shaking and fast draining after each rinse. This demineralization process took less than 30 minutes.

The demineralized bone fibers were soaked in a buffer to neutralize the pH of the demineralized bone fibers to a non-cytotoxic level (e.g., pH≥4). The demineralized bone fibers were press dried to remove excess liquid and remained in a moist state until further processing.

Example 3. Residual Calcium Content of Demineralized Bone Fibers

Figure 3:
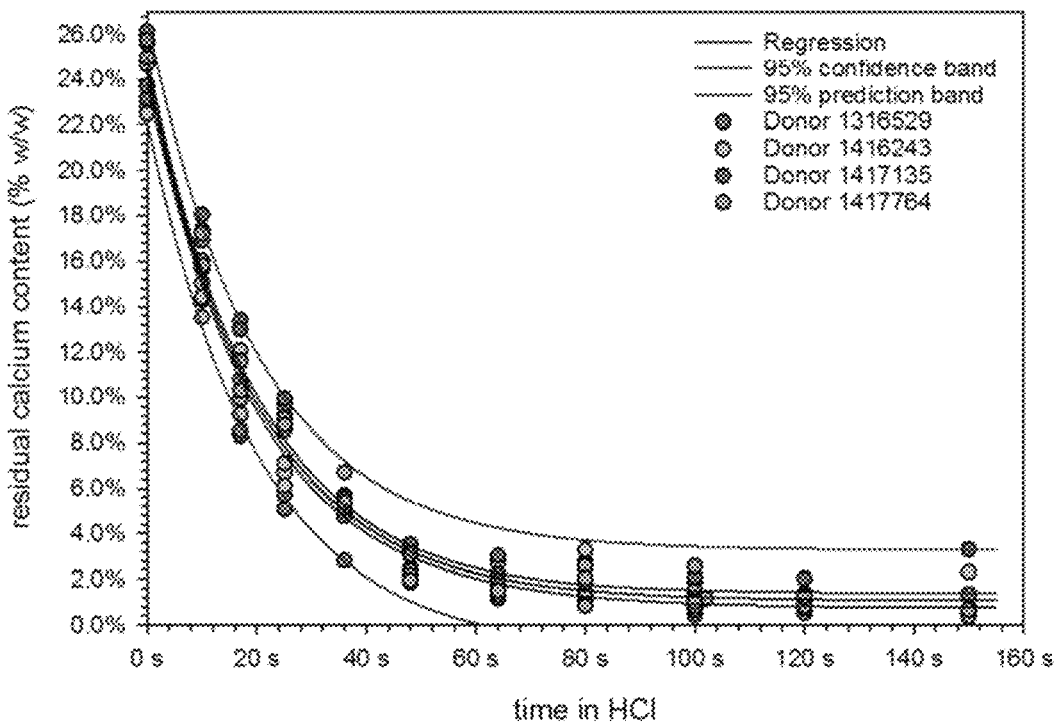
FIG. 3 shows residual calcium content (wt %) of demineralized bone fibers prepared with different acid exposure time periods.

CNC-milled bone fibers with target thickness of 0.009" and target length of 0.75" were generated from cortical bones using the method described in Example 1. The mineralized fibers were used to produce demineralized bone fibers according to the demineralized method described in Example 2. In particular, the mineralized fibers were exposed to 1 M HCl at 25 mL acid per gram of fibers. At the described times, a buffer was added. All samples were rinsed several times with water. The residual calcium content of the demineralized bone fibers was measured and plotted against the time of HCl exposure (FIG. 3). The residual calcium content decreased as the HCl exposure increased, and the residual calcium content decreased from about 20-27% to less than about 8% within 30 seconds.

Figure 4:
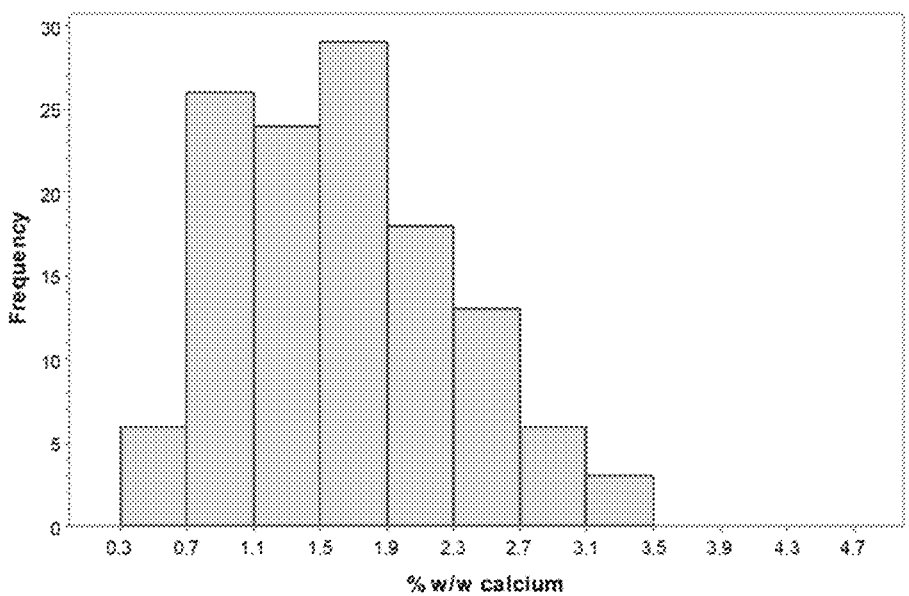
FIG. 4 shows residual calcium contents of demineralized bone fibers prepared with SPAD for an acid exposure time of about 120 seconds.

Example 4. Residual Calcium Content of Demineralized Bone Fibers Prepared with SPAD 125 samples of demineralized bone fibers from one donor were prepared as described in Example 2 with acid exposure for approximately 120 seconds and then tested for residual calcium content (FIG. 4). All 125 samples showed a residual calcium content of less than 4% while at least 110 samples exhibited a residual calcium content in the range of about 0.5-3%.

Figure 5:
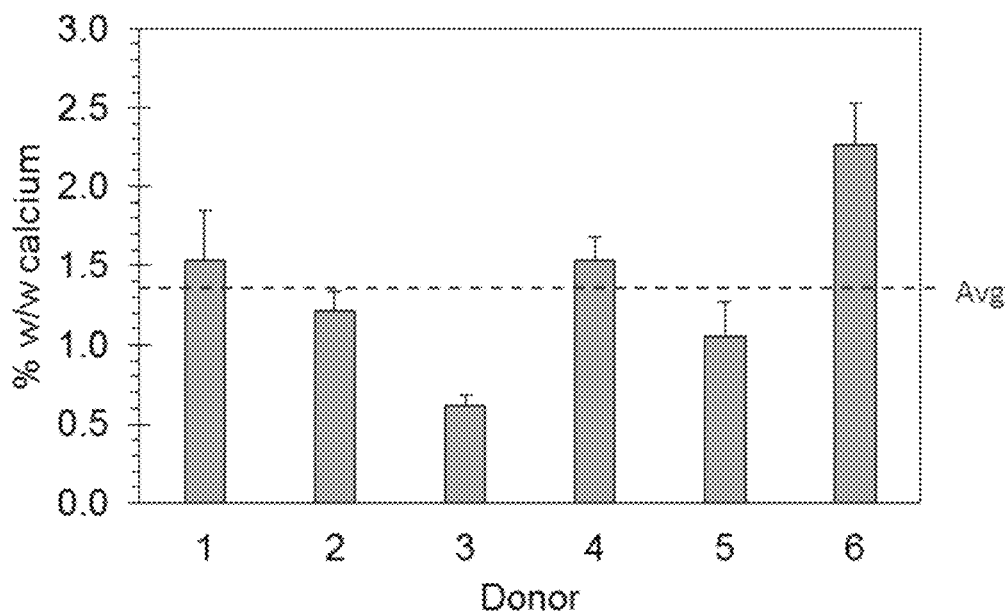
FIG. 5 shows residual calcium contents of demineralized bone fibers prepared with SPAD for an acid exposure time of about 140 seconds. The broken line represents the average residual calcium content.

Example 5. Residual Calcium Content of Demineralized Bone Fibers Prepared with SPAD Six representative samples were taken from demineralized bone fibers from six donors that were prepared as described in Example 2 with acid exposure for approximately 140 seconds and then tested for residual calcium content (FIG. 5). The average residual calcium content of the six samples across the six donors ranged from about 0.6-2.2%. The error bars represent the standard error. The broken line represents the average residual calcium content of about 1.4% among the six samples.

Example 6. Quantification of BMPs in Demineralized Bone Fibers

Samples were prepared as described in Example 8. Approximately 100 mg was weighed from each freeze-dried DBM (n=24). The samples were rehydrated with DMEM at a ratio of 1 mg freeze-dried DBM: 5 μL of DMEM. Purified collagenase (Worthington Biochemical, #CLSPA) was reconstituted with Dulbecco's modified Eagle minimum essential medium (DMEM) at 1446 U/mL. The reconstituted collagenase solution was added to the rehydrated DBM at a ratio of 1 mg freeze-dried DBM: 10 μL collagenase solution. The DBM was digested in the collagenase solution at 37° C. for 17±1 hours with vigorous shaking, followed by centrifugation and the supernatant were used in ELISA assays to quantify BMP-2 and BMP-7 extracted from demineralized bone fibers using Quantikine kits (R&D Systems, Inc. DBP200 and DBP700) according to the manufacturer instruction. The samples were run in triplicates.

Figure 6:
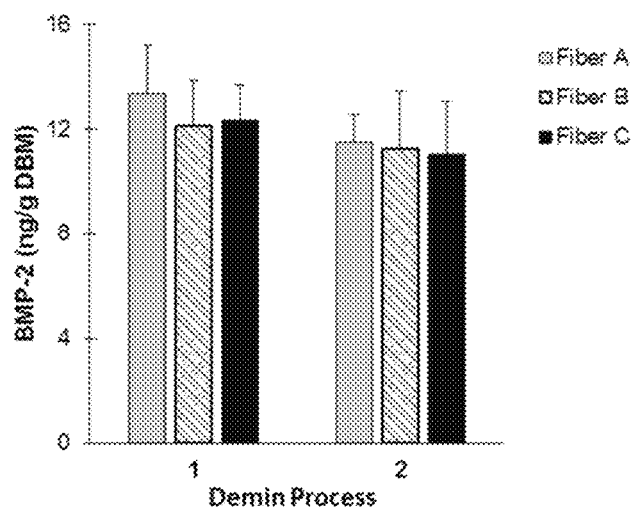
FIG. 6 shows quantification of BMP-2 extracted from demineralized bone fibers in ELISA assays. Demin Process 1=PAD process; Demin Process 2=SPAD process.
Figure 7:
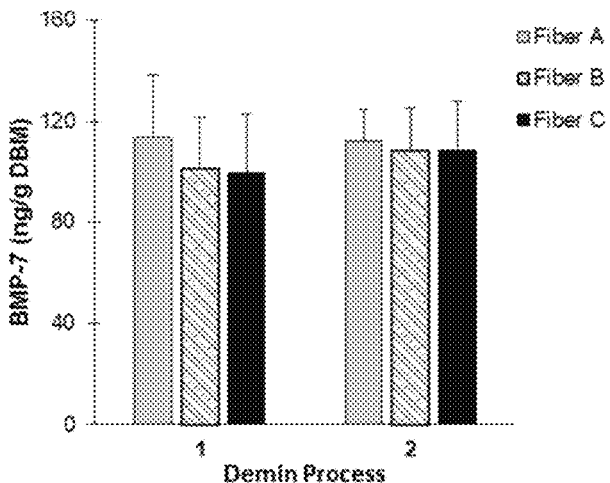
FIG. 7 shows quantification of BMP-7 extracted from demineralized bone fibers in ELISA assays. Demin Process 1=PAD process; Demin Process 2=SPAD process.
Figure 8:
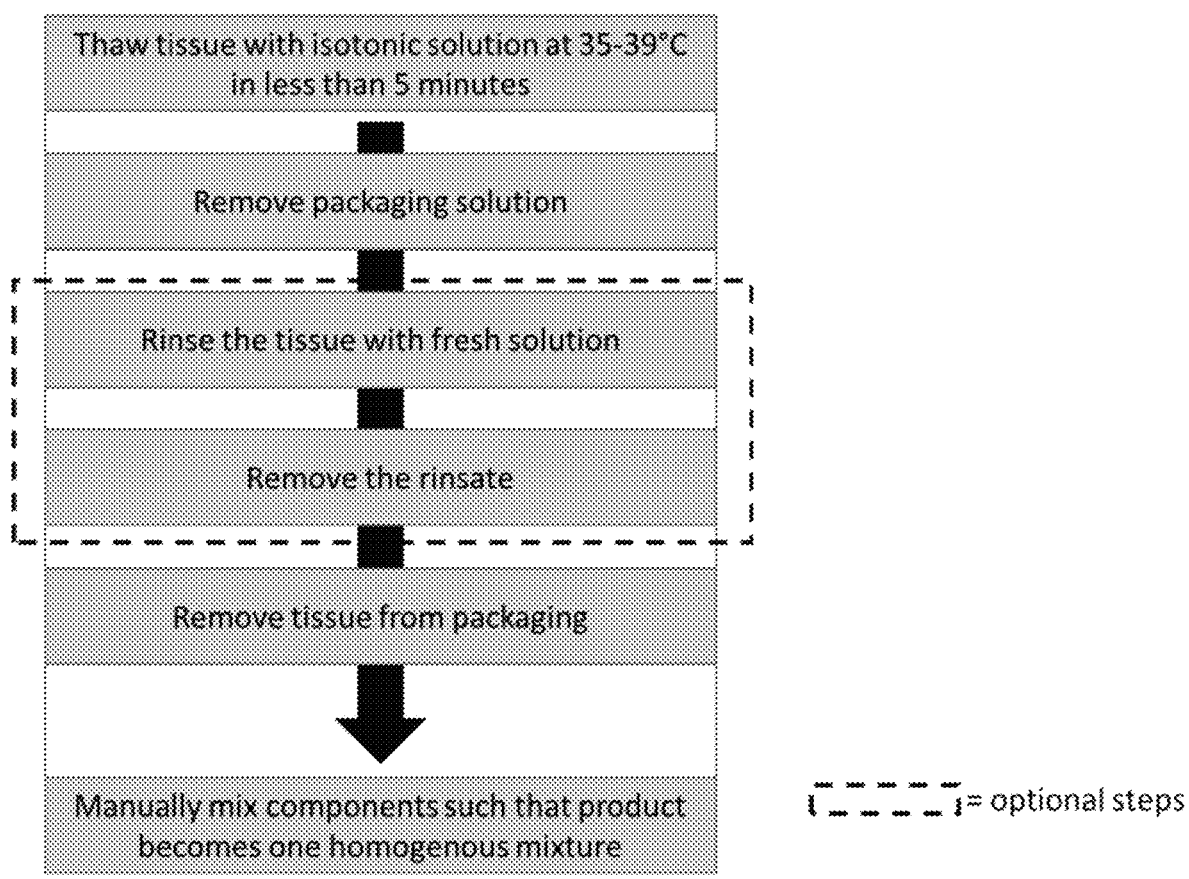
FIG. 8 shows steps for mixing demineralized bone fibers with a non-demineralized bone particulate containing viable bone cells.

Regardless of the fiber type and demineralization process used the DBM retained consistent BMP-2 and BMP-7 levels (FIGS. 6 and 7).

Example 7. Implant with Demineralized Bone Fibers

CNC-milled fibers with target thickness of 0.009" and target length of 0.75" were demineralized by exposing the bone fibers in 1 M HCl for approximately 120-140 seconds, then a buffer was added for approximately 60-80 seconds. After removal from the vessel, the samples were then further rinsed. Following demineralization, four individual implant samples were prepared to have 20-25 mg of the demineralized bone fibers, based on their dry weight. The four implant samples were freeze-dried and stored at an ambient temperature until ready for implantation. The assay chosen for evaluating the osteoinduction of the implant samples was the athymic nude mouse model. Here, each mouse received two implants, one in each biceps femoris and gluteus superficialis muscle pouch. Implant samples prepared from the same demineralization run were not implanted into the same mouse to ensure random distribution. Prior to implantation, the dried implant samples were thoroughly rehydrated with saline. Each individual implant sample was implanted into the muscle pouch within five minutes of rehydration. After 35 days, the mice were sacrificed and the implant material and surrounding tissue removed. The explant material was fixed with 10% formalin, decalcified, and bisected along the mid-sagittal plane parallel to the long axis of the implant, then embedded with paraffin. The material was sectioned at 4-6 μm thick and a total of 6 sections was generated for each implant sample. This provided a better representation of the proximal, middle, and distal portions of the implant site. All sections were stained with hematoxylin and eosin and evaluated for new bone elements. New bone elements were defined as: cartilage, chondrocytes, chrondroblasts, osteoblasts, osteocytes, osteoid, newly formed bone, or bone marrow. Scores were provided for each implant sample based on the percentage of new bone elements within the total implant area.

Example 8. CNC-Milling and Demineralization Processes for Cortical Fibers

Long cortical bones from twelve (n=12) donors were used for this study and stored at −80° C.

Recovered long bones were used to prepare bone segments in sets of three consecutive donors (e.g., donors 1-3 were processed at one time, donors 4-6 were processed at a later time, etc.). These segments were later used to produce computer numerical control (CNC)-milled cortical bone fibers representative of three different fiber technologies to achieve certain targeted fiber dimensions (Table 1).

TABLE 1

| CNC-milled cortical bone fibers | |
| --- | --- |
| Fiber type label | Targeted fiber dimensions |
| A | 0.50" length, 0.009" thickness |
| B | 0.50" length, 0.003" thickness |
| C | 0.75" length, 0.009" thickness |

Figure 9:
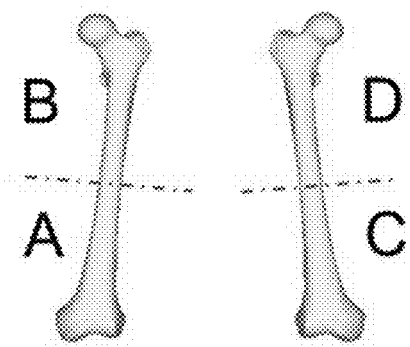
FIG. 9 shows a segmentation scheme for isolated long bone diaphysis. Paired femora from a single donor are shown. Each long bone diaphysis was cut to produce segments matching target lengths needed for downstream CNC milling. Each letter is a fiber type label corresponding to a different target fiber type as described in Table 1. A randomized segmentation scheme was generated for each donor. Within a donor, the same scheme was used to cut femora and tibiae.

Recovered tissues were moved from freezer storage to a 2-8° C. fridge and allowed to thaw for 1-3 days. Thawed long bones were debrided and cleaned. Each isolated diaphysis was then randomly assigned to produce two bone segments, with each segment assigned to one of the demineralized bone fiber technologies of interest. Isolated diaphyses were cut at specific points (identified using digital calipers) using a bandsaw to produce bone segments of lengths matching the target lengths for the three fiber types (Table 1). An example of the segmentation scheme is shown in FIG. 9. The letters designate different targeted fiber types described in Table 1.

The intramedullary contents of each bone segment were removed using a rasp, and the segments were lavaged with sterile water until the rinsate ran clear. Each segment was further cleaned.

Prepared bone segments were placed in separate bags and stored at −80° C. until ready to proceed with CNC milling.

Preparation of CNC-Milled Cortical Bone Fibers

Prepared bone segments were CNC-milled in batches of three consecutive donors (e.g., donors 1-3 were milled at one time to prepare batch 1, donors 4-6 were milled at a later time to prepare batch 2, etc.). These CNC-milled cortical bone fibers represent three different fiber types (Table 1).

After milling, the CNC-milled cortical fibers from the three donors milled simultaneously were carefully mixed together to produce a full batch of CNC-milled cortical fibers. CNC-milled cortical fibers from each batch were then separated into aliquots for two separate demineralization methods as well as for remaining mineralized fibers. All aliquots of CNC milled cortical fibers were stored at −80° C. until ready for demineralization or other experiments.

Demineralization of CNC-Milled Cortical Bone Fibers

Aliquots of CNC-milled cortical fiber batches underwent one of two separate demineralization methods. These demineralization methods are identified in Table 2. All CNC-milled fiber batches were removed from −80° C. storage and allowed to thaw at room temperature immediately before demineralization.

TABLE 2

Demineralization methods

| Demin. method label | Demin. method |
|---|---|
| 1 | PAD |
| 2 | SPAD |

For CNC-milled cortical fiber aliquots processed by demineralization method 1 (PAD), the Orbopad vessel with a flat filter was assembled and loaded with 40 mL 70% v/v isopropanol; this assembly was used for all three fiber types in order to harmonize processes across fiber types. The assembled vessel was placed on an orbital shaker set to 150 RPM for all incubation steps. A peristaltic pump was also calibrated prior to performing demineralization runs each day. A 50-g aliquot of CNC-milled cortical fibers from each batch was loaded into the vessel; a 4-L pulse of 0.5 M hydrochloric acid (HCl) was then pumped into the vessel, and the vessel was agitated for five minutes. HCl was drained from the vessel via peristaltic pumping, and the acid pulse was repeated once more. The fibers were then rinsed in a 3-L pulse of sterile water with agitation for five minutes, the vessel was drained, and the fibers were rinsed in a 3-L pulse of 0.1 M sodium phosphate buffer (pH 6.8-7.0) with agitation for five minutes. The sodium phosphate buffer was then drained from the vessel, and the buffer rinsate was confirmed to have a pH of 5.5-7.0 before completing the demineralization method. The fibers were rinsed in a final 3-L pulse of sterile water as before, the vessel was drained, and the fibers became demineralized bone fibers (also referred to herein as demineralized bone matrix (DBM) or DBM fibers) and were transferred from the vessel onto a 710 μm/125 μm sieve assembly. Excess moisture was pressed from the DBM fibers, the DBM fibers were transferred to an absorbent towel, and the DBM fibers were further press-dried. The press-dried DBM fibers were weighed and then separated into aliquots for residual calcium analysis, in vitro experiments, in vivo implantation, and bulk sample storage. All PAD DBM fiber aliquots were stored at −80° C. until ready for use.

For CNC-milled cortical fiber aliquots processed by demineralization method 2 (SPAD), the Orbopad vessel with an inner filter and an outer filter was assembled and placed on an orbital shaker set to 160 RPM for all incubation steps. A 3.4-L aliquot of 1.0 M HCl, 700 mL aliquot of 3.0 M sodium glycinate buffer, and four 4-L aliquots of saline (0.9% w/v NaCl in water) were prepared before each demineralization run. CNC-milled cortical fibers from each batch were sieved with a 710-μm sieve, and a 50-g aliquot of the sieved fibers were loaded into the vessel. The HCl aliquot was poured into the vessel via the vessel funnel cap, and the vessel was agitated for two minutes. The orbital shaker was stopped, and the sodium glycinate buffer aliquot was poured into the vessel; the vessel was then agitated for a further one minute. The orbital shaker was stopped once more, and solution was drained from the vessel via peristaltic pumping. The first aliquot of saline was poured into the vessel, the vessel was agitated for one minute and then stopped, and the saline was drained from the vessel. The saline rinse step was performed three additional times as before, with the exception that the fibers (now DBM fibers) and saline were decanted from the vessel onto a 710-μm sieve after the fourth saline rinse, rather than draining the vessel via peristaltic pumping. All runs were confirmed to have no more than 30 minutes elapsed between addition of HCl to the vessel and removal of the DBM fibers from the vessel. Excess moisture was pressed from the DBM fibers, the DBM fibers were transferred to an absorbent towel, and the DBM fibers were further press-dried. DBM fibers were then soaked in 50 mL Dulbecco's Modified Eagle Medium (DMEM) without agitation for five to ten minutes. DBM fibers were press-dried as before, and the DMEM rinsate was confirmed to have a pH≥4.0. The press-dried DBM fibers were weighed and then separated into aliquots for residual calcium analysis, in vitro experiments, in vivo Implantation, and bulk sample storage. All SPAD DBM fiber aliquots were stored at −80° C. until ready for use.

Example 9. Residual Calcium Analysis of DBM Fibers

DBM fibers (as described in Example 8) were analyzed for residual calcium contents in two studies.

Study 1.

Immediately before DBM fiber digestion, a 2-g sample of wet, press-dried DBM fibers from each of the n=24 PAD or SPAD DBM fiber preparations was placed in an aluminum pan, and the fibers comprising each sample were teased apart with forceps and spread into a thin layer across the surface of the pan. A sample of mineralized, ground bone meal supplied by the National Institute of Standards and Technology (NIST Standard Reference Material 1486, used as a control sample) was placed in a separate aluminum pan. The test and control samples were dried in a 110±5° C. drying oven at ambient pressure overnight (≥16 h) and then cooled to room temperature inside a desiccator cabinet. Six replicates of 100-130 mg dry tissue from each test sample, along with a single replicate of 100-130 mg dry tissue from the control sample, were weighed into microwave-assisted reaction system (MARS) Xpress vessels (CEM Corporation) and incubated in 8 mL of 1 M HCl at room temperature for 15 minutes. Following this, the digestion vessels were capped, and all samples were digested using the MARS (CEM Corporation). Samples were confirmed to have fully digested before continuing.

Following digestion, each sample was analyzed in duplicate for residual calcium content using working reagent prepared from the calcium (CPC) reagent kit (Eagle Diagnostics catalog no. 2400-1, prepared by mixing calcium base reagent and calcium color reagent in a 1:1 volume ratio). Sample or calcium analytical standard (50-150 μg mL$^{-1}$ calcium) was mixed with working reagent in a 1-cm cuvette at a volume ratio of 20 μL sample:2 mL working reagent. The cuvette contents were immediately measured at λ=570 nm. Test samples were measured undiluted; in cases where the sample absorbance was above the standard curve range, an aliquot of the digested test sample was diluted with ultrapure water and reanalyzed.

To calculate the residual calcium content of each sample, the calcium concentration of the digest was calculated from the standard curve and multiplied by the corresponding dilution factor (if needed). The calcium concentration in the digest was multiplied by the digest volume to calculate the mass of calcium in each digest, which was then divided by the total tissue mass to determine the calcium mass percentage of each sample (the residual calcium content). Altogether:

$$R = \frac{(A-I)*d*V}{(10^3 \text{ µg mg}^{-1})*S*(m-m_0)} \times 100\% \qquad \text{Equation 1}$$

where:
R is the residual calcium content (expressed as a mass percentage),
A is the measured absorbance of the digested sample,
I is the standard curve intercept, as determined by linear regression of the analytical standards,
d is the dilution factor of the assayed digest,
V is the digest volume, in mL,
S is the standard curve slope, in mL µg$^{-1}$, as determined by linear regression of the analytical standards, and
(m−m$_0$) is the mass, in mg, of the weighed dry DBM fibers (accounting for sample transfer loss, m$_0$).

The average residual calcium content of the 6 replicates for each sample (batch, fiber type, and demineralization process) was calculated and the frequency of those samples reaching a defined residual calcium content level was plotted. The average residual calcium content of the samples within each demineralization test group was calculated (n=12 per demineralization process) and determined to be 0.09±0.023 wt % for PAD DBM fiber samples versus 0.7±0.096 wt % for SPAD DBM fiber samples. It was determined using one-way ANOVA that there was a statistical difference between these two demineralization groups (p<0.0001).

Study 2.

Residual calcium testing was performed on samples of two products containing CNC-milled fibers demineralized by two distinct processes: demin A (PAD) and demin B (SPAD). The average residual calcium content of each sample was reported (n=15 demin A, n=434 demin B) as 0.4±0.14 wt % for demin A and 2.0±0.05 wt % for demin B and a statistical difference was noted when completing one-way ANOVA analysis (p<0.001).

Example 10. Compression Testing of DBM Fibers

DBM fiber samples having been stored at −80° C. without freeze-drying after demineralization (referred to as non-freeze-dried DBM fibers) and DBM fibers freeze-dried post-demineralization and stored at room temperature (referred to as freeze-dried DBM fibers) (as described in Example 8) were both assessed via compression testing. Non-freeze-dried DBM fiber samples were simply moved from −80° C. storage to 2-8° C. storage and allowed to thaw overnight before testing, while freeze-dried DBM fiber samples were required to be rehydrated before compression testing. In order to rehydrate the freeze-dried DBM fiber samples, 15 mL DMEM (Life Technologies catalog no. 21063029) were added to each sample (containing 5 g press-dried DBM fibers before freeze-drying) contained within a 50-mL conical tube; the DBM fibers were then allowed to soak in DMEM at room temperature and without agitation for 10 minutes. The sample tubes were then inverted to ensure complete wetting of the DBM fiber samples and allowed to soak for a further 10 minutes. The rehydrated DBM fiber samples were transferred to individual absorbent towels and press-dried similarly to the process performed at the end of demineralization. The rehydrated, press-dried DBM fiber samples were returned to separate 50-mL conical tubes and stored at 2-8° C. until ready to perform compression testing.

To prepare DBM fiber aliquots for compression testing (referred to as DBM anvils), DBM fibers from each of the samples were packed to a volume of approximately 1 cc using a 5-cc disposable syringe cut at the 0-cc demarcation via bandsaw, adding DBM fibers to or removing DBM fibers from the syringe as necessary to achieve the appropriate aliquot size. After carefully extruding the cylindrical DBM anvil from the syringe and ensuring it consisted of one cohesive mass, the height and diameter of each anvil were measured using digital calipers. In order to prevent sample drying, DBM anvils were returned to containers with their respective remaining (moist) DBM fibers until ready to perform compression testing.

Compression testing of each moist DBM anvil was performed following a method from literature and using a dual column universal testing system (Instron model no. 3367) equipped with a 50 N static load cell (Instron catalog no. 2530-437) (Meng et al., *Sci. Rep.* 5 (17802), 2015, pp 1-14). A 0.01 N preload was first applied to the anvil, and the anvil was then compressed to 50% strain at a rate of 0.05 mm s$^{-1}$. Compression data was collected at a rate of 2 Hz using Instron Bluehill software. The compression data was used to produce a stress-strain plot for each of the n=48 total DBM fiber samples (counting both freeze-dried and non-freeze-dried DBM), and the elastic modulus of each sample was determined via linear regression of data up to 10% strain.

Figure 10:
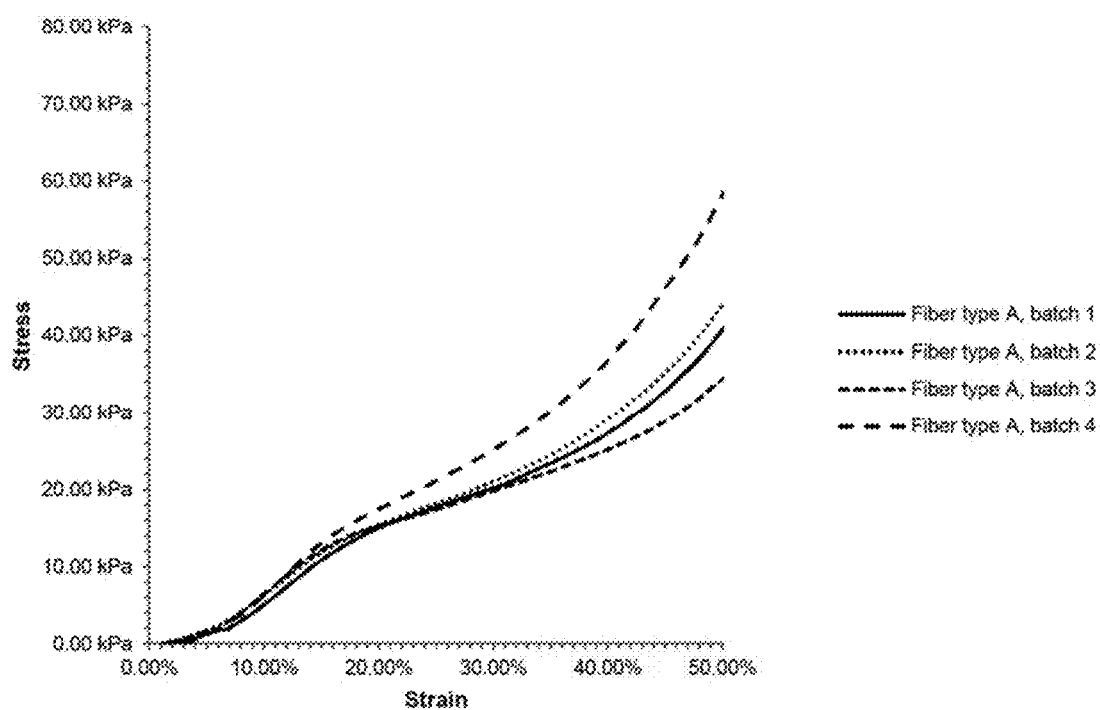
FIG. 10 shows compressive stress-strain curves for representative freeze-dried DBM fiber samples prepared from fiber type A with demineralization method 2 (SPAD process). Similar curves were generated for DBM fiber samples from other fiber types, demineralization methods, and freeze-dried status. Data from 0-10% strain were used to determine the elastic modulus of each DBM fiber sample.

Compression data were used to produce stress-strain plots for non-freeze-dried and freeze-dried DBM fibers from each of the n=48 total DBM fiber samples. A representative set of stress-strain curves are shown in FIG. 10.

The elastic modulus of each DBM fiber sample was calculated by performing a linear regression on the sample's stress-strain curve for data from 0-10% strain. A two-way ANOVA was independently run for the non-freeze-dried DBM fiber and freeze-dried DBM fiber datasets to determine the influence of fiber type and demineralization method on DBM fiber elasticity within each dataset. Within the dataset for the n=24 non-freeze-dried DBM fiber samples, no significant interaction was observed between fiber type and demineralization method on elastic modulus, $F(2,18)=0.48$, $p=0.626$. Analysis of main effects illustrated that fiber type did not influence the elastic modulus ($F(2,18)=2.29$, $p=0.130$) while demineralization method did influence the elastic modulus ($F(1,18)=33.69$, $p<0.001$). Within the dataset for the n=24 freeze-dried DBM fiber samples, no significant interaction or main effects were observed for fiber type and demineralization method with respect to the sample's elastic modulus: $F(2,18)=0.140$, $p=0.871$ for the two-way interaction; $F(2,18)=0.73$, $p=0.496$ for the fiber type main effect; and $F(1,18)=0.52$, $p=0.480$ for the demineralization method main effect.

Figure 11:
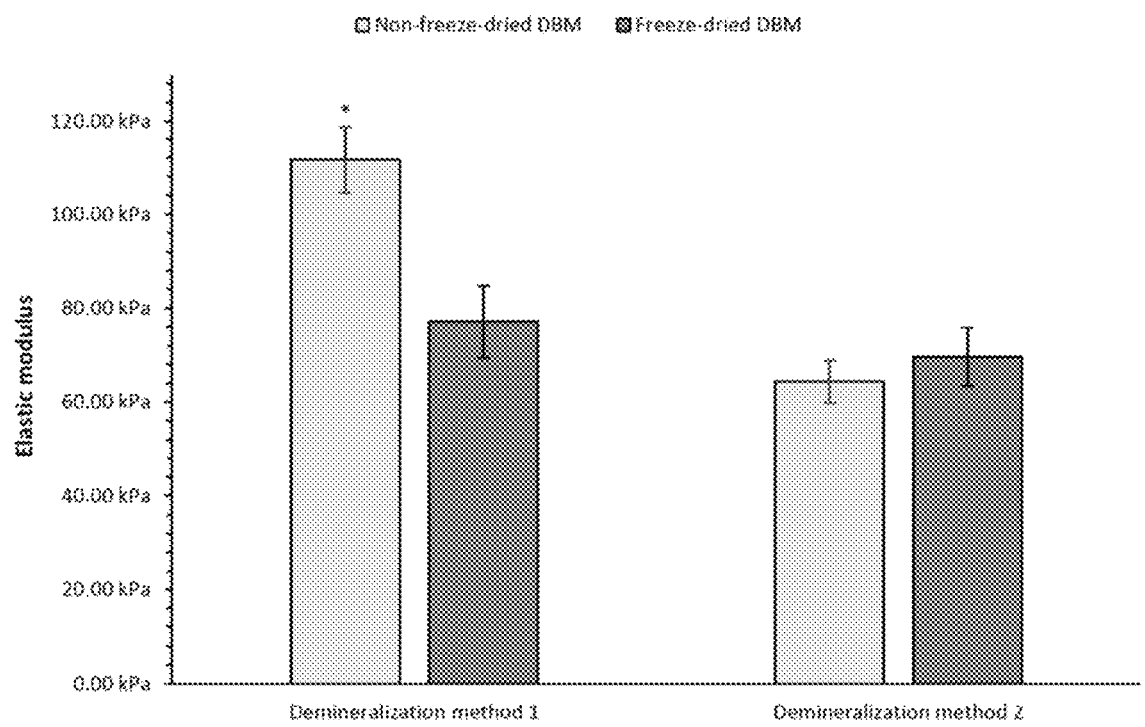
FIG. 11 shows influence of demineralization method and freeze-drying on the elastic modulus of DBM fibers. Bars represent the average±standard error of n=12 replicates (across donor batches and fiber types) for each DBM fiber preparation method. The elastic modulus of non-freeze-dried DBM fibers prepared by demineralization method 1 was significantly higher than that of the other three DBM fiber preparation types (*, $p \leq 0.003$). Elastic moduli were calculated from the 0-10% strain data on the stress-strain curves using a linear regression model. Demineralization method 1=PAD process; demineralization method 2=SPAD process.

An additional two-way ANOVA was run on the combined dataset to determine the influence of demineralization method and freeze-drying on DBM fiber elasticity. A significant interaction between the effects of demineralization method and freeze-drying on the elastic modulus was observed, F(1,44)=9.46, p=0.004. A post-hoc Tukey pairwise comparison confirmed that DBM fibers prepared by demineralization method 1 and freeze-dried was significantly higher than the other three DBM fiber preparations (p≤0.003), which were not significantly different from one another. These results are reported in Table 3 and shown in FIG. 11.

TABLE 3

Elastic modulus of DBM fibers

| Demin. method | Freeze-dried? | Average | S.E.M. |
|---|---|---|---|
| 1 | No | 111.64 kPa | 7.12 kPa |
| 1 | Yes | 77.10 kPa | 7.65 kPa |
| 2 | No | 64.38 kPa | 4.50 kPa |
| 2 | Yes | 69.62 kPa | 6.15 kPa |

The reported average and standard error of the mean (S.E.M.) for each DBM preparation is derived from n = 12 replicates across donor batches and fiber types. Elastic moduli were calculated from the 0-10% strain data on the stress-strain curves using a linear regression model.

The reported average and standard error of the mean (S.E.M.) for each DBM preparation is derived from n=12 replicates across donor batches and fiver types. Elastic moduli were calculated from the 0-10% strain data on the stress-strain curves using a linear regression model.

Example 11. Osteoinductive Potential Properties of DBM Fibers

Figure 12:
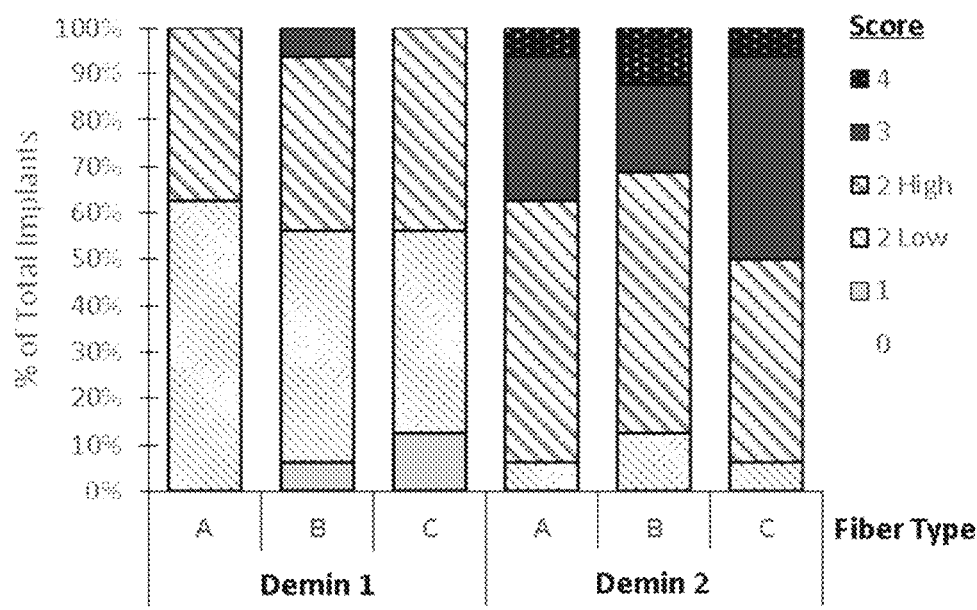
FIG. 12 shows osteoinductivity (OI) scores per demin group and fiber type evaluated. Six slides were analyzed per implant sample and the highest score of the six slides was reported. A. The percentage of total implants was calculated by using the scores of the four implanted replicates for each of the four batches for a total of sixteen implants per treatment group. B. Scores from all replicates of all batches and fiber types were pooled together to calculate the percentage of implants that had a defined percentage of new bone elements from the total implant area and compared between the two demineralization processes (n=48 per demin process). Demin 1=PAD process; Demin 2=SPAD process.
Figure 12:

This study was designed to evaluate the osteoinductive potential of multiple samples following implantation in the muscle of the athymic mouse for 35 days in order to understand the impact of processing changes to the measure of osteoinductive potential. Each freeze-dried sample contained 20-25 mg PAD (Demin 1) or SPAD (Demin 2) DBM fibers prepared as described in Example 8, was rehydrated with 0.9% saline, and then implanted inter-muscularly into an athymic nude mouse. Each DBM fiber sample (n=24) was implanted as 4 replicates for a total of 96 samples. After 35 days, the implant material and surrounding tissue were removed from the intermuscular pouch of athymic nude mice. Each sample was histologically prepared, 6 consecutive slides were prepared from each sample, stained for H&E, and then evaluated for evidence of new bone formation, which includes the presence of bone marrow, new lamellar bone, osteoblasts, osteocytes, chondroblasts, chondrocytes, and cartilage. Of the 6 slides per sample, the highest score was reported (FIG. 12). Scores were determined by the percentage of new bone elements from the total implant area (Table 4). The frequency of a specific score being given to each implant within each fiber type and demineralization sample group was calculated and presented as a percentage (FIG. 12A). The scores from the fiber types were pooled together for each demineralization process and presented as percentage of total implants with a certain percentage of new bone elements detected (FIG. 12B).

TABLE 4

Scoring of osteoinductive potential per implant site

| Grade | Estimated Cross Sectional Area |
|---|---|
| 0 | No implant present |
| 1 | Implant present; no evidence of new bone formation |
| 2 Low | >0 to 5% evidence of new bone formation |
| 2 High | 6 to 25% evidence of new bone formation |
| 3 | 26 to 50% evidence of new bone formation |
| 4 | 51 to 100% evidence of new bone formation |

The average OI score of four replicates of each fiber type samples was calculated for each sample (Table 5). The score difference was calculated between the sample that was prepared from the same donor batch and fiber type but underwent either Demin Process 1 or 2 and represented here as numerical. The Wilcoxon signed-rank statistical test was performed on the score differences and a statistically significant increase in the average 01 score of DBM fibers that had undergone Demin Process 2 (SPAD) rather than Process 1 (PAD) (W=45.0, p=0.009 was detected.

TABLE 5

The average OI score

| Fiber type | Donor batch | Avg OI Score Demin 1 | Avg OI Score Demin 2 | Score difference (Demin 2 − 1) |
|---|---|---|---|---|
| A | 1 | 2.00 | 2.00 | 0.00 |
| A | 2 | 2.00 | 2.50 | 0.50 |
| A | 3 | 2.00 | 2.50 | 0.50 |
| A | 4 | 2.00 | 2.75 | 0.75 |
| B | 1 | 2.00 | 2.75 | 0.75 |
| B | 2 | 2.25 | 2.25 | 0.00 |
| B | 3 | 2.00 | 2.50 | 0.50 |
| B | 4 | 1.75 | 2.25 | 0.50 |
| C | 1 | 1.50 | 2.25 | 0.75 |
| C | 2 | 2.00 | 3.25 | 1.25 |
| C | 3 | 2.00 | 2.75 | 0.75 |
| C | 4 | 2.00 | 2.00 | 0.00 |

Figure 13:
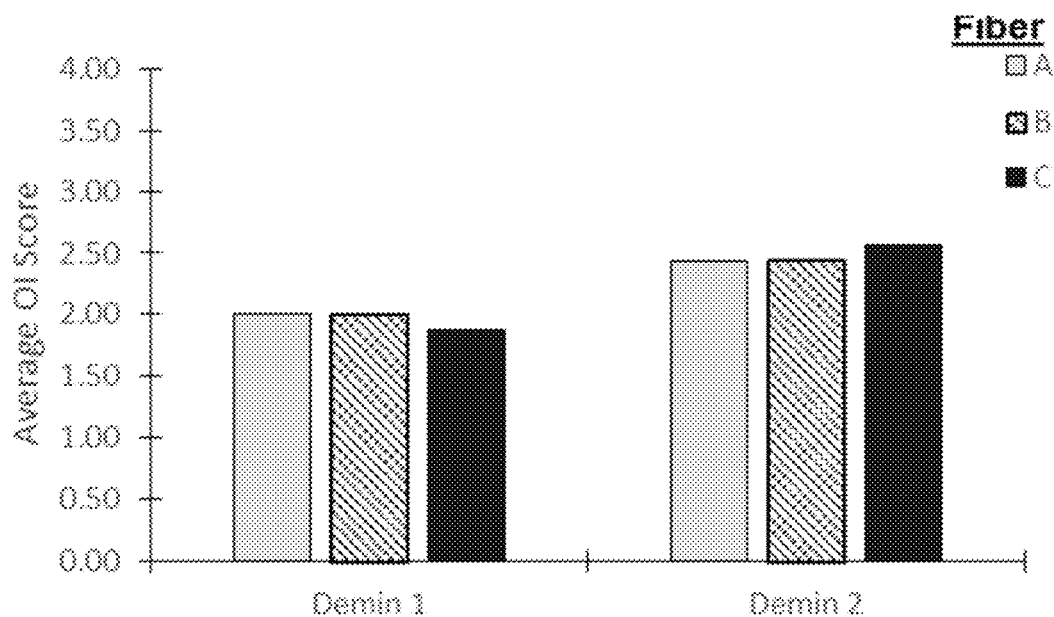
FIG. 13 shows average OI Scores per Demin group evaluated. The average OI score was calculated for each of the fiber types in each demineralization group for a total of 16 implants per group. Demin 1=PAD process; Demin 2=SPAD process.

The Wilcoxon signed-rank test determined that there was a statistically significant increase in the average OI score when CNC-milled cortical fibers were demineralized by Demin 2 (SPAD) compared to by Demin 1 (PAD) (Table 5, FIG. 13). There was no significant difference between the Fiber Types within each Demin method.

Example 12. Growth Factor Content of DBM Fibers

The growth factor content in DBM fibers can influence the performance of the DBM fibers upon implantation. However, in addition to the quantity of the growth factors, the kinetic release of the growth factors from the DBM fibers and the functionality of those proteins play a vital role in the performance upon implantation. DBM fibers were prepared as described in Example 8. BMP elution from PAD or SPAD DBM fibers was analyzed using an BMP-7 ELISA kit (R&D systems) over a period of 7 days. Each time point contained twenty-four samples each weighing 25±1 mg. The twenty-four samples represented the two different demineralization processes, three different mineralized fiber groups, and four different batches of processed tissue from pools of donors. After weighing the freeze-dried DBM, each sample was rehydrated with 300 mL DMEM and placed into a transwell with a membrane pore size of 0.4 µm in wells of a 24-well plate with each well containing 1 mL of DMEM. All samples were incubated at 37° C. for 5% $CO_2$ for up to 7 days. At the indicated time points, the transwell was removed and the remaining media in the well was collected and measured.

Figure 14:
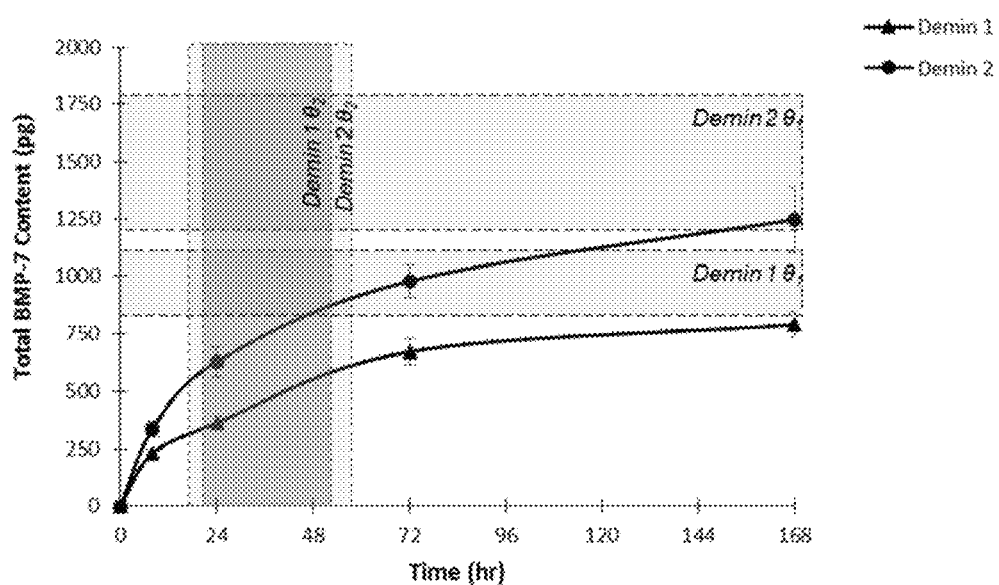
FIG. 14 shows total BMP-7 content eluted from DBM fiber samples over time.

Triplicates of each sample of the collected media were tested following the manufacturer's protocol for BMP-7 (R&D Systems) at a 1:7 dilution factor. The BMP-7 concentration was determined based on a 4-point parameter logistic curve plotted with the standard curve values. This was converted into a total BMP-7 content amount based on the volume of media collected at that given time point in the experiment. Averages of the data from the 12 sample groups per demineralization process were generated to understand the BMP-7 content eluted at the indicated time points over 7 days (average±SEM represented by the solid black lines) (FIG. 14). The best-fit curve of the dataset was generated using the Michaelis-Menten equation which provided $\theta_1$ and $\theta_2$ parameters. The $\theta_1$ and $\theta_2$ values were calculated along with their 95% confidence intervals (shaded boxes with dashed lines). Here, $\theta_1$ represents the maximum BMP-7 content that could be eluted from the DBM fibers over time; whereas, $\theta_2$ can be defined as the time in which the BMP-7 content is half of the maximum amount of elution dictated by $\theta_1$.

The data indicate that BMP-7 elutes from DBM fiber samples prepared by either Demin Process 1 or 2 at a similar rate ($\theta_2$). However, there is a statistically significant increase in the amount of BMP-7 that eluted during the 7 day timeframe ($p<0.05$) from DBM fibers prepared by Demin Process 2 versus Demin Process 1 (as seen by non-overlapping $\theta_1$ ranges in the figure). It is important to note that BMP-7 is not stable over extended periods of time and therefore values measured at later time points could be a combination of both BMP-7 eluting from the DBM fibers as well as previously eluted BMP-7 becoming degraded.

Example 13. Induction of Cell Proliferation by DBM Fibers

Aliquots of the n=24 prepared DBM fiber samples (as described in Example 8) were used to assay the ability of DBM fibers to induce cellular proliferation in a C2C12 Immortalized mouse myoblast cell line (ATCC catalog no. CRL-1772). Cells were expanded in a growth medium comprised of DMEM (ATCC catalog no. 30-2002; 4.5 g L$^{-1}$ glucose, 1 mM sodium pyruvate, 4 mM L-glutamine, 1.5 g L$^{-1}$ sodium bicarbonate, and 15 mg L$^{-1}$ phenol red) and supplemented with 10% v/v fetal bovine serum (FBS; ATCC catalog no. 30-2020), 100 U mL$^{-1}$ penicillin, and 100 µg mL$^{-1}$ streptomycin (Thermo-Fisher Scientific catalog no. 15140-122). Cells were then seeded at 25,000 cells cm$^{-2}$ into individual wells of four HTS Transwell 24-well plates (Corning catalog no. 3397) and allowed to attach for five hours.

While cells were attaching, triplicate 20-25 mg aliquots of each freeze-dried DBM fiber sample were weighed and rehydrated for one minute with 2 mL of a low-serum medium comprised of DMEM supplemented with 1% FBS, 100 U mL$^{-1}$ penicillin, and 100 µg mL$^{-1}$ streptomycin. Rehydrated DBM fiber samples were aseptically press-dried and transferred to the 0.4-µm pore polycarbonate permeable support of the HTS Transwell plates; an additional 300 µL low-serum medium was then added to the DBM.

After attaching to the culture plates, C2C12 cells were switched into the low-serum medium in order to reduce cellular proliferation. The permeable supports containing DBM fibers were returned to the HTS Transwell plates in order to expose cells to any soluble factors present in the DBM. Triplicate wells of each culture plate were designated as a positive control and exposed to 150 ng mL$^{-1}$ recombinant human bone morphogenetic protein 2 (rhBMP-2; R&D Systems catalog no. 355-BM-050/CF) in low-serum medium in lieu of DBM; a further three wells of each culture plate were designated as a negative control and exposed to low-serum medium without DBM fibers or other additives. All culture plates were incubated at 37° C. in a humidified atmosphere of 5% CO$_2$ for six days with a single medium change occurring after three days of incubation. Images of the cells were taken on days 1, 3, and 6.

After C2C12 cells had been exposed to DBM fibers for six days, all culture plates were chilled on ice, rinsed three times with 1 mL ice-cold Dulbecco's phosphate-buffered saline (DPBS), and lysed in 1 mL ice-cold lysis buffer consisting of 0.5% v/v Triton X-100 in DPBS with added Halt protease inhibitor cocktail (Thermo-Fisher Scientific catalog no. 78425). Culture plates were sealed with Parafilm, frozen at −80° C., and quickly thawed in a 37° C. water bath. The surface of each well was scraped with a pipette tip, and the lysate in each well was thoroughly mixed by pipetting. The culture plates then underwent an additional two freeze-thaw cycles as before (without well scraping or mixing). After the third freeze-thaw cycle, lysates were transferred to low-binding microcentrifuge tubes and spun at 17,500×g for 5 minutes at 4° C.; the clarified lysates were then transferred to new low-binding tubes.

The protein content of each cell lysate was measured in triplicate by the bicinchoninic acid (BCA) assay using a commercially-available kit (Thermo-Fisher Scientific catalog no. 23225). Lysates were mixed with the BCA reagent as specified in the kit instructions, incubated at 37° C. for 30 minutes, and allowed to cool. The absorbance of the lysates was then measured at $\lambda=562$ nm. Absorbance measurements were converted to protein concentrations using a standard curve prepared from bovine serum albumin and lysis buffer.

Figure 15:
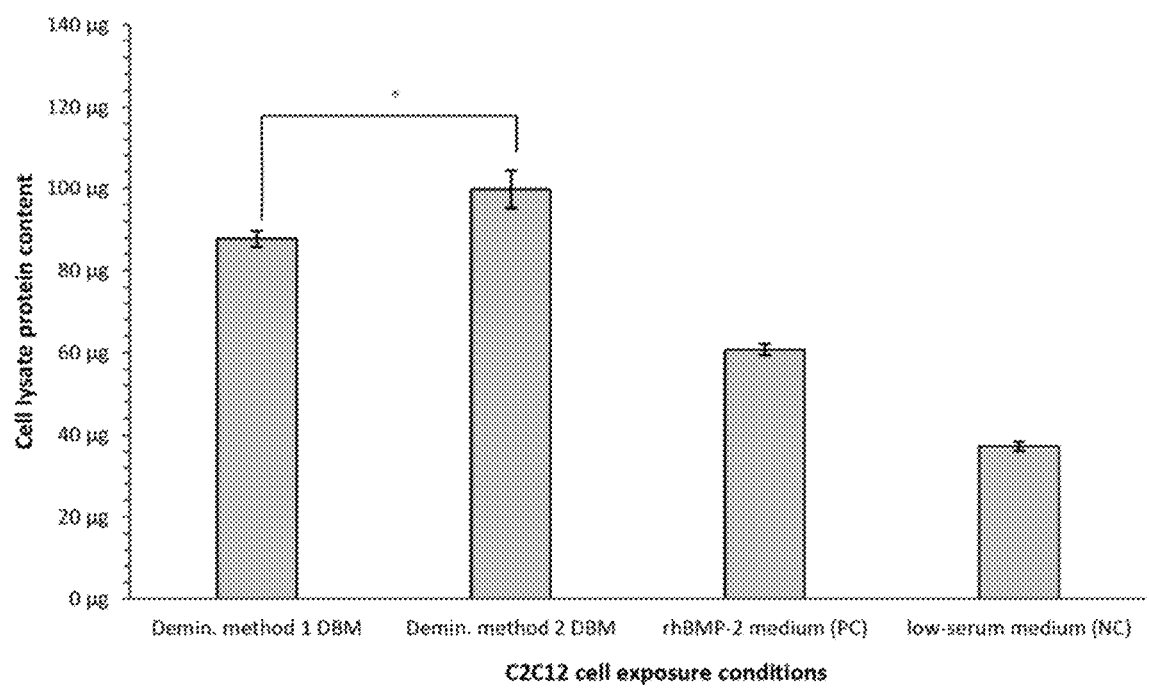
FIG. 15 shows protein content of cell lysates from C2C12 cells exposed to DBM, rhBMP-2, or low-serum medium. Cells were either exposed to 20-25 mg rehydrated DBM fibers produced by demineralization method 1 (PAD) or 2 (SPAD), 150 ng mL-1 rhBMP-2 in low-serum medium (positive control, PC), or low-serum medium alone (negative control, NC) for six days. Each bar represents the average±S.E.M. protein content of the resulting cell lysates (n=9 for DBM fiber groups, n=3 for control groups). A significant difference was identified in the protein content of lysates derived from cells exposed to DBM fibers produced by demineralization method 1 vs 2 (*, p=0.049).

A two-way ANOVA was run on the dataset for three culture plates to determine the influence of fiber type and demineralization method on the protein content of the induced C2C12 cells. 18 protein content measurements were included in the statistical analysis. No significant interaction was observed between fiber type and demineralization method on cellular protein content, $F(2,12)=0.55$, $p=0.593$. Analysis of main effects illustrated that fiber type did not influence the cellular protein content ($F(2,12)=0.31$, $p=0.742$) while demineralization method did influence the cellular protein content ($F(1,12)=4.79$, $p=0.049$); thus, C2C12 cells exposed to DBM fibers produced by demineralization method 2 yielded cell lysates with a significantly higher protein content than that of cells exposed to DBM fibers produced by demineralization method 1. Cell lysates from all DBM-exposed groups also contained significantly higher protein content than the lysates of cells exposed to 150 ng mL$^{-1}$ rhBMP-2 (positive control) or low-serum medium alone (negative control). The protein content of all cell lysates is shown in FIG. 15.

Total protein content is frequently used as a metric for cell quantity, and so the increased protein content of cells exposed to DBM fibers may be indicative of increased proliferation. The higher protein content of lysates derived from cells exposed to DBM fibers produced by demineralization method 2, as compared to lysates derived from cells exposed to DBM fibers produced by demineralization method 1, may indicate that DBM fibers from demineralization method 2 contains a higher amount, more accessible form, or more active form of one or more mitogenic proteins.

Interestingly, increased cell proliferation was qualitatively seen by microscopy over the six days of cellular exposure to DBM, rhBMP-2, or low-serum medium. Over the course of six days of DBM fiber exposure, C2C12 cells rapidly expand, even going so far as to grow on top of one another (apparent on day 6 by the cross-hatched appearance toward the center of the image). Qualitatively similar trends were seen in cells exposed to DBM fibers produced by demineralization methods 1 and 2. By comparison, some proliferation is evident in the positive control group exposed to rhBMP-2, but this increase in cell quantity over the course of six days is considerably less dramatic than that seen from DBM-exposed cells. Proliferation is least apparent in the negative control group, where cells were exposed only to low-serum medium, a finding which is consistent with low-serum medium's purpose of discouraging proliferation.

Morphological changes upon exposure to DBM fibers were observed. Upon exposure to DBM, C2C12 cell morphology became more elongated and fibroblast-like, consistent with osteoprogenitor cells, while cells exposed to rhBMP-2 quickly assumed the characteristic cobblestone shape of osteoblasts. Cells exposed only to low-serum medium spontaneously fused to form multinucleated myotubes, as expected of confluent C2C12 cells not stimulated to differentiate. Cells under low-serum media conditions were not likely to proliferate. However, cells in low-serum media with DBM had increased cell confluency over the 6 days compared to the rhBMP-2 and low-serum only controls. Cells in the negative control group spontaneously fused to form multinucleated myotubes, as indicated for this cell type as the myoblasts approach confluency. The changes in the negative control group may therefore be considered the natural fate of this cell type. Cells in the positive control group, however, quickly deviated from the natural fate and assumed the cobblestone appearance of committed osteoblasts. Cells exposed to DBM fibers (whether produced by demineralization method 1 or 2) also deviated from the negative control and exhibited a change toward a potentially fibroblastic morphology, aligning with each other and even appearing to grow on top of one another as confluency was reached. It appears that DBM-exposed cells may have assumed an osteoprogenitor phenotype.

All documents, books, manuals, papers, patents, published patent applications, guides, abstracts, and/or other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed:

1. A method for preparing a demineralized bone graft, wherein the demineralized bone graft has a residual calcium content of less than 6 wt % based on the dry weight of the demineralized bone graft, comprising subjecting a non-demineralized bone graft to a single incubation in an acid solution for no more than 300 seconds, wherein the acid solution has a pH of 0-4.

2. The method of claim 1, wherein the non-demineralized bone graft comprises bone fibers, bone particles, bone sheets, bone cubes, bone shafts, or a combination thereof.

3. The method of claim 1, wherein the non-demineralized bone graft comprises non-demineralized bone fibers, and wherein the demineralized bone graft comprises demineralized bone fibers.

4. The method of claim 3, wherein the demineralized bone fibers are osteoinductive.

5. The method of claim 3, wherein the non-demineralized bone fibers have an average shortest dimension of less than 200 μm.

6. The method of claim 3, wherein the demineralized bone fibers have an elastic modulus of less than 100 kPa.

7. The method of claim 3, further comprising adding an effective amount of a buffer to the acid solution after the single incubation.

8. The method of claim 3, further comprising storing the demineralized bone fibers at room temperature.

9. The method of claim 3, further comprising drying the demineralized bone fibers.

10. The method of claim 3, further comprising releasing at least 75 wt % of calcium in the non-demineralized bone fibers.

11. The method of claim 3, further comprising retaining at least 1 ng of a bone morphogenetic protein (BMP) per gram of the non-demineralized bone fibers, based on the dry weight of the non-demineralized bone fibers, wherein the BMP is selected from the group consisting of BMP-2, BMP-3, BMP-4, BMP-5, BMP-6, BMP-7, BMP-8, BMP-9, BMP-10, BMP-11, BMP-12, BMP-13, BMP-14, BMP-15 and a mixture thereof.

12. The method of claim 3, wherein the non-demineralized bone fibers are generated by a Computer Numerical Control (CNC) machine using a chip load of 0.004"-0.011".

13. A composition comprising the demineralized bone fibers produced by the method of claim 3.

14. A composition comprising demineralized bone fibers having a residual calcium content of between 0.5-6 wt % based on the dry weight of the demineralized bone fibers, wherein the demineralized bone fibers are osteoinductive, wherein the demineralized bone fibers have a specific area 185-5,550 $cm^2/g$, and wherein the demineralized bone fibers are combined with and stored in glycerol.

15. The composition of claim 14, wherein the demineralized bone fibers have an average shortest dimension of less than 200 μm.

16. The composition of claim 14, wherein the demineralized bone fibers have a specific surface area of at least 200 $cm^2/g$.

17. The composition of claim 14, wherein the demineralized bone fibers have an elastic modulus of less than 100 kPa.

18. An implant comprising the composition of claim 14.

19. The implant of claim 18, further comprising a synthetic material.

20. The implant of claim 18, further comprising a bone particle or particulate.

21. A method for treating a tissue or organ defect in a subject, comprising applying to a site of the defect an effective amount of the composition of claim 14.

22. A method for preparing a demineralized bone graft, wherein the demineralized bone graft has a residual calcium content of less than 6 wt % based on the dry weight of the demineralized bone graft, comprising subjecting a non-demineralized bone graft to a single incubation in an acid solution for no more than 300 seconds, wherein the acid solution has a pH of 0-4 and the demineralized bone graft is combined with and stored in glycerol.

23. The method of claim 22, wherein the non-demineralized bone graft comprises bone fibers, bone particles, bone sheets, bone cubes, bone shafts, or a combination thereof.

24. The method of claim 22, wherein the non-demineralized bone graft comprises non-demineralized bone fibers, and wherein the demineralized bone graft comprises demineralized bone fibers.

25. The method of claim 24, wherein the demineralized bone fibers are osteoinductive.

26. The method of claim 24, wherein the non-demineralized bone fibers have an average shortest dimension of less than 200 μm.

27. The method of claim 24, wherein the demineralized bone fibers have an elastic modulus of less than 100 kPa.

28. The method of claim 24, further comprising adding an effective amount of a buffer to the acid solution after the single incubation.

29. The method of claim 28, wherein the pH of the resulting solution is adjusted to 2.5-7 within 90 seconds after the addition of the buffer.

30. The method of claim 24, further comprising storing the demineralized bone fibers at room temperature.

31. The method of claim 24, further comprising drying the demineralized bone fibers.

32. The method of claim 24, further comprising releasing at least 75 wt % of calcium in the non-demineralized bone fibers.

33. The method of claim 24, further comprising retaining at least 1 ng of a bone morphogenetic protein (BMP) per gram of the non-demineralized bone fibers, based on the dry weight of the non-demineralized bone fibers, wherein the BMP is selected from the group consisting of BMP-2, BMP-3, BMP-4, BMP-5, BMP-6, BMP-7, BMP-8, BMP-9, BMP-10, BMP-11, BMP-12, BMP-13, BMP-14, BMP-15 and a mixture thereof.

34. The method of claim 24, wherein the non-demineralized bone fibers are generated by a Computer Numerical Control (CNC) machine using a chip load of 0.004"-0.011".

35. A composition comprising the demineralized bone fibers produced by the method of claim 24.

\* \* \* \* \*